(12) United States Patent (10) Patent No.: US 8,420,078 B2
Eisenbach et al. (45) Date of Patent: Apr. 16, 2013

(54) METHODS AND IMMUNOGENIC CELL PREPARATIONS FOR TREATING ANTIGEN-ASSOCIATED DISEASES

(75) Inventors: Lea Eisenbach, Rechovot (IL); Arthur Machlenkin, Kiryat-Ekron (IL); Adrian Paz, Petach-Tikva (IL); Boaz Tirosh, Brighton, MA (US); Esther Tzehoval, Nes-Ziona (IL)

(73) Assignee: Yeda Research and Development Co. Ltd., Rehovot (IL)

( * ) Notice: Subject to any disclaimer, the term of this patent is extended or adjusted under 35 U.S.C. 154(b) by 789 days.

(21) Appl. No.: 11/885,871

(22) PCT Filed: Feb. 21, 2006

(86) PCT No.: PCT/IL2006/000218
§ 371 (c)(1), (2), (4) Date: Aug. 12, 2008

(87) PCT Pub. No.: WO2006/095330
PCT Pub. Date: Sep. 14, 2006

(65) Prior Publication Data
US 2010/0129410 A1 May 27, 2010

Related U.S. Application Data

(60) Provisional application No. 60/659,948, filed on Mar. 10, 2005.

(51) Int. Cl.
*A61K 35/14* (2006.01)
(52) U.S. Cl.
USPC ........................ 424/93.71; 424/573
(58) Field of Classification Search .................. None
See application file for complete search history.

(56) References Cited

U.S. PATENT DOCUMENTS 5,788,963 A * 8/1998 Murphy et al. ............ 424/93.21
6,652,848 B1 11/2003 Gong et al.
2005/0214268 A1* 9/2005 Cavanagh et al. ......... 424/93.21
2006/0024691 A1* 2/2006 Benz ................................. 435/6

FOREIGN PATENT DOCUMENTS
WO WO 2004/053072 * 6/2004

OTHER PUBLICATIONS

Nestle, 1998, Nature Medicine, 4(3): 328-332.*
McDonald et al, 2000 (FASEB Journal,14(6): A946, abstract only).*
Triozzi et al, 2000, Cancer, 89(12): 2646-2654.*
Schuler-Thurner et al, 2002, J Exp Med, 195(10) : 1279-1288.*
Gazzaniga et al, 2001, J Invest Dermatol, 116: 664-671.*
Sallusto et al, 1994, J Exp Med, 179: 1109-1118.*
Triozzi et al (Cancer, 2000, vol. 89, pp. 2647-2654).*
Abstract of Kumagi et al (International Journal of Oncology, 2003, vol. 23, pp. 949-955).*
Lutz et al (Journal of Immunological Methods, 1999, vol. 223, pp. 77-92).*
Kim et al (International Journal of Cancer, May 1, 2004, vol. 109, pp. 685-690).*
Jalili et al (Clinical Cancer Research, 2004, vol. 10, pp. 4498-4508).*
Geiger et al (Cancer Research, Dec. 2001, vol. 61, pp. 8513-8519).*
Rehman et al (Journal of Endourology, Oct. 2003, vol. 17, pp. 647-657).*
The abstract of Ohnishi et al (Radiology, 1994, vol. 193, pp. 747-752).*
Geiger et al (The Lancet, 2000, vol. 356, pp. 1163-1165).*
Response Dated Jun. 3, 2010 to Office Action of Jan. 5, 2010 From the Israel Patent Office Re.: Application No. 185725.
International Preliminary Report on Patentability Dated Sep. 20, 2007 From the International Bureau of WIPO Re.: Application No. PCT/IL2006/000218.
Candido et al. "Local Administration of Dendritic Cells Inhibits Established Breast Tumor Growth: Implications for Apoptosis-Inducing Agents", Cancer Research, 61:228-236, Jan. 2001.
Chen et al. "Combined Radiation Therapy and Dendritic Cell Vaccine for Treating Solid Tumors With Liver Micro-Metastasis", Journal of Gene Medicine, 7:506-517, 2005.
Figdor et al. "Dendritic Cell Immunotherapy: Mapping the Way", Nature Medicine 10(5):475-480, May 2004.
Gallucci et al. "Natural Adjuvants: Endogenous Activators of Dendritic Cells", Nature Medicine, 5(11):1249-1255, Nov. 1999.
Javadpour et al. "Failure of Cryosurgical Treatment of Experimental Intradermal Tumors to Eradicate Microscopic Lymph Node Metastases in Guinea Pigs", Jnci, 62(6):1479-1481, Jun. 1979.
Kikuchi et al. "Tumor Regression Induced by Intratumor Administration of Adenovirus Vector Expressing CD40 Ligand and Naive Dendritic cells", Cncer Research, 60:6391-6395, Nov. 2000.
McIlroy et al. "Optimizing Dendritic Cell-Based Anticancer Immunotherapy: Maturation State Does Have Clinical Impact", Cancer Immunol Immunother, 52:583-591, 2003.
Melero et al. "Intratumoral Injection of Bone-Marrow Derived dendritic Cells Engineered to Produce Interleukin-12 Induces Complete Regression of Established Murine Transplantable Colon Adenocarcinomas", Gene Therapy, 6:1779-1784, 1999.
Sauter et al. "Consequences of Cell Death: Exposure to Necrotic Tumor cells, But Not Primary Tissue Cells or Apoptotic Cells, Induces the Maturation of Immunostimulatory Dendritic Cells", J. Exp. Med., 191(3):423-433, Feb. 2000.
Shin et al. "Antitumor Effect of Intratumoral Administration of Dendritic Cell Combination With Vicristine Chemotherapy in a Murine Fibrosarcoma Model", Histol Histopathol, 18:435-447, 2003.

(Continued)

*Primary Examiner* — Karen Canella

(57) ABSTRACT

A method of inhibiting growth of, reducing or eliminating a cell population of a subject in need thereof is disclosed. The method comprises (a) thermally, mechanically and/or chemically damaging antigen-bearing cells which comprise at least one antigen characterizing cells of the cell population, with the proviso that the chemically damaging of the antigen-bearing cells is not predominantly effected using one or more antineoplastic agents, thereby generating immunogenic cells; and (b) introducing in the subject a cell aggregate which comprises the immunogenic cells and added antigen-presenting cells, thereby inducing an immune response for inhibiting growth of, reducing or eliminating the cell population of the subject.

14 Claims, 4 Drawing Sheets

OTHER PUBLICATIONS

Tennenbaum et al. "Radiotherapy Potentiates the Therapeutic Efficacy of Intratumoral Dendritic Cell Administration", Cancer Research, 63:8466-8475, Dec. 2003.

Urano et al. "Antitumor Effects of Residual Tumor After Cryoablation: the Combined Effect Residual Tumor and a Protein-Bound Polysaccharide on Multiple Liver Metastases in a Murine Model", Cryobiology, 46:238-245, 2003.

Yamashita et al. "Enhanced Tumor Metastases in Rats Following Cryosurgery of Primary Tumor", Gann, 73:222-228, Apr. 1982.

Office Action Dated Jan. 5, 2010 From the Israel Patent Office Re.: Application No. 185725 and Its Translation Into English.

Office Action Dated Dec. 26, 2010 From the Israel Patent Office Re.: Application No. 185725 and Its Translation Into English.

Response Dated Nov. 14, 2010 to Office Action of Jul. 14, 2010 From the Israel Patent Office Re.: Application No. 185725.

Office Action Dated Jul. 14, 2010 From the Israel Patent Office Re.: Application No. 185725 and Its Translation Into English.

Daro et al. "Comparison of the Functional Properties of Murine Dendritic Cells Generated In Vivo With FLT3 Ligand, GM-CSF and FLT3 Ligand Plus GM-CSF", Cytokine, 17(3): 119-130, Feb. 7, 2002.

Koch et al. "Antigen Processing in Populations of Mature Murine Dendritic Cells is Caused by Subsets of Incompletely Matured Cells", The Journal of Immunology, 155: 93-100, 1995.

Machlenkin et al. "Combined Dendritic Cell Cryotherapy of Tumor Induces Systemic Antimetastatic Immunity", Clinical Cancer Research, 11(13): 4955-4961, Jul. 1, 2005.

Zola et al. "CD Molecules 2005: Human Cell Differentiation Molecules", Blood, 106: 3123-3126, 2005.

Avigan et al. "Fusion Cell Vaccination of Patients With Metastatic Breast and Renal Cancer Induces Immunological and Clinical Responses", Clinical Cancer Research, 10: 4699-4708, 2004. Abstract, Experimental Design, Lines 1, 2, p. 4699, Right Col., 2nd, 3rd §.

Maier et al. "Vaccination of Patients With Cutaneous T-Cell Lymphoma Using Intranodal Injection of Autologous Tumor-Lysate-Pulsed Dendritic Cells", Blood, 102(7): 2338-2344, 2003. Abstract, Lines 3-9, p. 2239, Right Col., Lines 11-16, p. 2340, Right Col., Results, Lines 1-5.

Nestle et al. "Dendritic-Cell-Based Therapeutic Vaccination Against Cancer", Current Opinion in Immunology, 17: 163-169, 2005.

\* cited by examiner

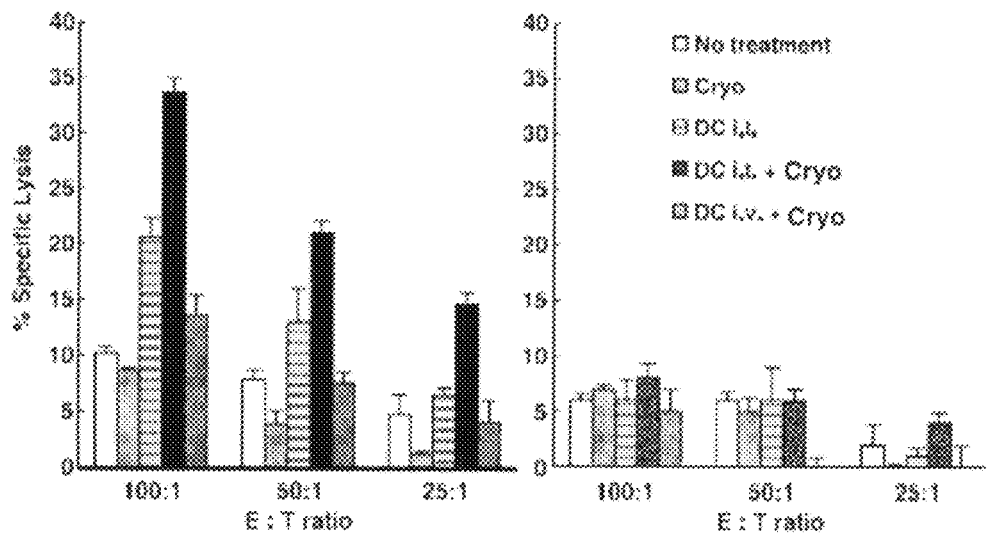
Fig. 1a Fig. 1b
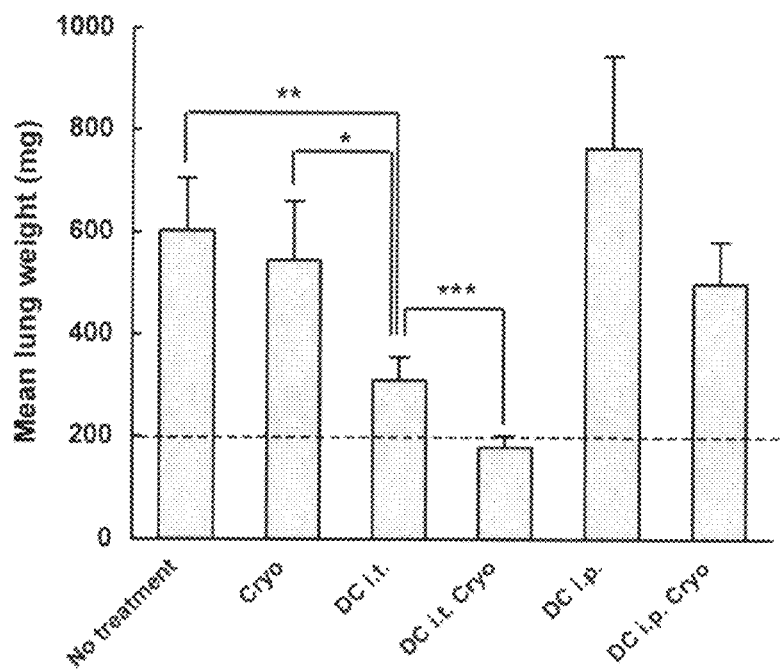
Fig. 2

METHODS AND IMMUNOGENIC CELL PREPARATIONS FOR TREATING ANTIGEN-ASSOCIATED DISEASES

RELATED APPLICATIONS

This Application is a National Phase of PCT Patent Application No. PCT/IL2006/000218 having International Filing Date of Feb. 21, 2006, which claims the benefit of U.S. Provisional Patent Application No. 60/659,948 filed on Mar. 10, 2005. The contents of the above Applications are all incorporated herein by reference.

FIELD AND BACKGROUND OF THE INVENTION

The present invention relates to methods of reducing, growth-inhibiting or eliminating a cell population of a subject in need thereof, to therapeutic cell preparations for practicing such methods and to methods of obtaining such cell preparations. More particularly, the present invention relates to methods of using combined localized cell ablation, such as cryoablation, and vaccination with antigen-presenting cells (APCs), such as dendritic cells, for treating a patient having a disease, such as a metastatic cancer, whose pathology involves a pathological cell population which is characterized by at least one antigen. The present invention further particularly relates to therapeutic cell preparations which comprise immunogenic aggregates of antigen-bearing cells and antigen-presenting cells which are capable of inducing in a subject in need thereof an immune response against a pathological cell population, such as a metastatic cancer cell population, which is specifically associated with at least one antigen.

Malignancies, such as lung and skin cancer, represent a large group of highly debilitating and/or lethal diseases constituting a primary cause of death, and an enormous social and economic burden in the Western world. In particular, cancer now constitutes the leading cause of death in the U.S. of people under the age of 85. The primary cause of lethality of malignant diseases such as lung and skin cancer arises from metastatic spread. In many cases, it is not possible to prevent the onset of metastatic disease since cancers are often metastatic by the time of diagnosis, and even in cases where cancers are diagnosed prior to this stage, complete surgical removal or destruction of primary lesion tissues which are capable of eventually generating metastases may not be feasible. Metastatic disease may be impossible to diagnose at early stages due to the small size of metastatic lesions, and/or the absence of reliable markers in primary lesions upon which to reliably predict their existence. Such lesions may be difficult/impossible to treat via ablative methods due to their being inaccessible, disseminated, and/or poorly localized. Chemotherapy/radiotherapy, the current methods of choice for treatment of certain metastatic malignancies are often ineffective or suboptimally effective, and have the significant disadvantage of being associated with particularly harmful and/or potentially lethal side-effects.

Thus, there exists a longstanding and urgent need for more effective, safer and less invasive methods of treating cancer.

Localized tumor ablation methods, such as cryoablation (i.e. tissue destruction by freeze-thawing), which can be catheter-based, are optimally effective, and minimally harmful/invasive for tumor treatment relative to chemotherapy/radiotherapy since they can be used to destroy cancerous tissues with optimal selectivity and with minimal harmful local/systemic side-effects. Cryoablation is effectively employed for the management of localized, accessible dermatological tumors, hepatocellular carcinoma, renal and prostate tumors, and hepatic colorectal metastases (Han K R, Belldegrun A S., 2004. BJU Int. 93:14-8; Johnson D B and Nakada S Y., 2003. J Endourol 17:627-32; Adam R. et al., 2004. Surg Clin North Am 84:659-71). Compared to surgical excision, catheter cryoablation, by virtue of being less invasive, results in reduced mortality and morbidity, and of being practicable on outpatients, which dramatically decreases treatment cost. In the case of hepatic colorectal metastases, the use of cryosurgery improves the percentages of resectability (Adam R. et al., 2004. Surg Clin North Am 84:659-71). A comparative study on domestic pigs has shown that cryoablation of renal parenchyma is superior to other necrosis-inducing ablations such as microwave thermoablation, radiofrequency energy and chemoablation by ethanol, hypertonic saline and acetic acid gels, in terms of reproducibility, consistency in size and shape, and the ability to monitor by ultrasound (Rehman J. et al., 2004. J. Endourol. 18:83-104). The mechanisms of cryoablation are multifactorial yet they culminate in necrotic cell death secondary to direct mechanical cellular damage induced by ice crystals; and vascular and endothelial injury with eventual ischaemia [Hoffmann N E, Bischof J C., 2002. Urology 60 (2 Suppl 1):40-9]. Freezing-induced immunostimulatory effects have been hypothesized to contribute to the therapeutic effects of cryosurgery, and although a few animal models and clinical case studies contradictorily describe either inhibition (Ablin R J. et al., 1973. Urology 2:276-9), or promotion (Yamashita T., et al., 1982. Gann. 73:222-8) of metastasis/tumor growth following primary tumor cryoablation, the majority of studies prove that cryoablation has no effect on subsequent tumor/metastasis development [Hoffmann N E, Bischof J C., 2002. Urology 60 (2 Suppl 1):40-9]. The main drawback of cryoablation, therefore, is that apart from its local effect on tumors, it does not elicit a systemic anti-cancer response to preclude metastasis.

Immunotherapeutic cancer treatment methods, such as those involving APC vaccination, have the potential to be optimally effective for treatment of inaccessible, disseminated, microscopic, recurrent and/or poorly localized lesions, such as metastatic lesions. One promising immunotherapy avenue involves the use of professional APCs, such as dendritic cells (DCs), to elicit systemic anti-cancer immunity. Dendritic cells are crucially important in antigen capture, processing and presentation to the effector arm of the immune system. Mature dendritic cells direct T-lymphocyte differentiation into effector or memory cells; induce natural killer (NK) cell activation, and induce B-cell differentiation into antibody-forming cells (Ardavin C. et al., 2004. Immunity 20:17-23). A potential role for dendritic cells in eliciting anti-tumor immunity was highlighted by the observation that increased density of dendritic cells present within a tumor correlates with an improved prognosis, and that migration of dendritic cells from the vicinity of the tumor to the draining lymph nodes is essential for the induction of anti-tumor immunity (Tsujitani S. et al., 1992. Int Surg. 77:238-41). Indeed, the potential of dendritic cell administration as an adjuvant treatment capable of potentiating immune-mediated resistance to cancer is supported by many animal experiments as well as initial human trials (Steinman R M, Dhodapkar M., 2001. Int J Cancer 94:459-73). Intratumoral dendritic cell administration has been shown to be potentially therapeutically useful, for example in the treatment of brain tumors (U.S. Patent Application No. 20040057935 to Yu et al.).

Combined radioablation and intratumoral dendritic cell administration has been successfully employed for treating solid tumors with liver micro-metastasis (Chen Z. et al., J Gene Med. 2004 Dec. 6; [Epub ahead of print]), or for treating melanoma or sarcoma tumors in mice (Teitz-Tennenbaum S. et al., 2003. Cancer Res. 63:8466-75). Similarly combined vincristine chemotherapy and intratumoral dendritic cell administration has been successfully employed for treating fibrosarcoma in mice (Shin J Y. et al., 2003. Histol Histopathol. 18:435-47). Such methods, however, are associated with the inherent disadvantages of radiotherapy and chemotherapy. Thus, while immunotherapies involving APC vaccination holds the promise of enabling effective induction of anticancer immunity, such an approach has failed to achieve satisfactory/optimal treatment of numerous types of cancer in humans. Use of combined radiotherapy or chemotherapy and intratumoral dendritic cell administration for treatment of cancer has also been suggested for treatment of brain tumors (U.S. Patent Application No. 20040057935 to Yu et al.).

Dying cells, particularly necrotic cells, which can be generated using localized tumor ablation methods such as cryoablation, are known to be a potent inducer of maturation of dendritic cells capable of inducing specific immunity against cells which express the same antigens as such dying cells (Gallucci S. et al., 1999. Nat. Med. 5:1249-55). Thus, in view of the capacity of localized tumor ablation methods, such as tumor cryoablation, to treat accessible localized tumors, such as bulky primary tumors, while generating dying cells, and in view of the capacity of APCs, which is potentiated by dying cells, to systemically eradicate inaccessible, disseminated and/or poorly localized lesions, such as metastatic lesions, microscopic lesions or recurrent lesions, a potentially optimal cancer treatment strategy would be is to combine such complementary methods so as to achieve treatment of both local and systemic lesions. Such a strategy has the great advantages of avoiding or minimizing the undesirable side-effects inherent to chemotherapy or radiotherapy, and of being practicable using minimally invasive, and broadly mastered techniques, such as catheter cryoablation, and administration of a cancer subject's own APCs.

Several prior art approaches have been employed or suggested in order to treat cancer using APC vaccination combined with tumor cryoablation.

One approach involves treating tumor cells with high temperature, isolating a lysate from the treated cells, and pulsing dendritic cells with the lysate in an attempt to obtain dendritic cells potentially suitable for therapeutic administration to a subject having such a tumor (PCT Publication No. WO/04 018659 to Goletz et al.).

Another approach involves freeze-thawing murine thymoma cells (Galea-Lauri J. et al., 2004. Cancer Immunol Immunother. 53:963-77), human metastatic renal cell carcinoma cells (Gitlitz B J. et al., 2003. J. Immunother. 26:412-9), or human colorectal cancer cells (Bremers A J. et al., 2000. Int J Cancer 88:956-61), and pulsing dendritic cells with lysate of the freeze-thawed cells in an attempt to obtain dendritic cells potentially suitable for therapeutic administration to a subject having such a thymoma, renal cell carcinoma, or colorectal cancer, respectively.

Still another approach involves freeze-thawing tumor cells, preparing soluble antigen from the freeze-thawed cells, and exposing cytokine-induced killer (CIK) cells to the soluble antigen in the presence of dendritic cells, in an attempt to generate activated anti-tumor CIK cells potentially suitable for therapeutic administration to a subject having such a tumor (Yu J. et al., 2003. Beijing Da Xue Xue Bao. 35:141-2).

An additional approach involves freeze-thawing human monoblastoid tumor cells, exposing dendritic cells to the freeze-thawed tumor cells, and then co-culturing the dendritic cells with T-lymphocytes in an attempt to generate proliferating immunostimulated anti-tumor T-lymphocytes potentially suitable for therapeutic administration to a subject having such a monoblastoid tumor (Rad et al., 2003. Cancer Res. 63:5143-5150).

Yet an additional approach involves genetically modifying human melanoma cells to express viral fusogenic membrane glycoprotein (FMG) so as to generate syncitia of tumor cells, freeze-thawing the tumor cell syncitia, isolating released exosomes therefrom, and exposing dendritic cells to the isolated exosomes in an attempt to achieve tumor antigen loading of the dendritic cells, and hence generation of dendritic cells potentially suitable for therapeutic administration to a subject having such a melanoma (Bateman A R. et al., 2002. Cancer Res. 62:6566-6578).

Still an additional approach involves, boiling or freeze-thawing murine thymoma cells, exposing dendritic cells to the boiled or freeze-thawed cells, and then co-culturing the dendritic cells with T-lymphocytes specific for an antigen specifically expressed by the tumor cells in an attempt to generate activated anti-thymoma T-lymphocytes potentially suitable for therapeutic administration to a subject having such a thymoma (Strome S E. et al., 2002. Cancer Res. 62:1884-9).

A further approach involves freeze-thawing murine fibrosarcoma cells (Cohen P J. et al., 1994. Eur J. Immunol. 24:315-9), or human B-lymphoblastoid leukemia cells (Herr W. et al., 2000. Blood 96:1857-1864), pulsing dendritic cells with lysate of the freeze-thawed cells, and co-culturing the pulsed dendritic cells with T-lymphocytes in an attempt to generate activated anti-tumor T-lymphocytes potentially suitable for therapeutic administration to a subject having such a fibrosarcoma, or B-lymphoblastoid malignancy, respectively.

All of the prior art approaches, however, suffer from significant disadvantages. For example, approaches requiring harvesting of tumor cells and/or immune effector cells; genetic modification of tumor cells; in-vitro thermal treatment of tumor cells, in-vitro preparation of subcellular or molecular components of tumor cells; in-vitro treatment of APCs with tumor cells or subcellular or molecular components thereof; and/or in-vitro treatment of APCs with immune effector cells are excessively complex, cumbersome and/or impractical to perform. Approaches involving attempts to generate in-vitro activated anti-tumor immune cytotoxic cells potentially suitable for therapeutic administration, have clearly and explicitly failed to achieve generation of such activated cells. Approaches involving loading of dendritic cells with exosomes isolated from freeze-thawed tumor cell syncitia in an attempt to achieve tumor antigen loading of the dendritic cells have failed to achieve such loading, and hence have failed to achieve generation of dendritic cells potentially suitable for cancer treatment. Approaches involving administration to a human metastatic renal cell carcinoma patient of dendritic cells pulsed with lysate of freeze-thawed tumor cells of the patient have failed to achieve satisfactory/optimal therapeutic efficacy. Approaches involving co-culturing of T-lymphocytes of a colorectal cancer patient with autologous dendritic cells pulsed with a lysate of freeze-thawed tumor cells of the patient in an attempt to generate immunostimulated T-lymphocytes directed against the tumor cells have not attempted administration of such T-lymphocytes to the patient, and hence have failed to demonstrate any therapeutic efficacy. Similarly, approaches involving co-culturing of T-lymphocytes with autologous dendritic cells pulsed with a lysate of freeze-thawed autologous human transformed B-lymphoblastoid cells in an attempt to generate immunostimulated T-lymphocytes directed against the transformed cells have not attempted administration of such T-lymphocytes to a patient bearing such transformed cells, and hence have also failed to demonstrate any therapeutic efficacy. Approaches involving exposure of tumor cells to high temperatures are disadvantageous in that such temperatures tend to denature polypeptides/peptides and epitopes thereof involved in optimal induction of anti-tumor immunity. As well, in the in-vivo context, high temperature treatment of tissues is suboptimal or undesirable relative to low temperature treatment for various reasons. For example, relative to low temperature treatment, high temperature treatment of tissues may be associated with excessive blood loss, thrombogenic risk, and/or patient discomfort,. Furthermore, for treatment of various conditions, high temperature treatment of tissues is far less easily and/or routinely performed by the medical practitioner than cryoablation which is a widely mastered treatment modality. In certain contexts, cryoablation may be advantageously repeated to treat disease relapse, whereas repeated high temperature treatment is contraindicated.

Thus, all prior art approaches have failed to provide an adequate solution for treating diseases such as cancer using combined APC vaccination and localized cell ablation, such as tumor cryoablation.

There is thus a widely recognized need for, and it would be highly advantageous to have, a method of treating diseases such as cancer devoid of the above limitation.

SUMMARY OF THE INVENTION

The present invention discloses the use of combined cell-/tissue-damaging treatment such as cryoablation and in-situ administration of antigen-presenting cells into pathological tissue for killing/damaging of such tissues for treatment of diseases, such as solid tumors, whose pathology is associated with such tissues. This use can be effected in a variety of ways as further described and exemplified hereinbelow.

According to one aspect of the present invention there is provided a method of inhibiting growth of, reducing or eliminating a cell population of a subject in need thereof, the method comprising (a) thermally, mechanically, and/or chemically damaging antigen-bearing cells which comprise at least one antigen characterizing cells of the cell population, with the proviso that the chemically damaging of the antigen-bearing cells is not predominantly effected using one or more antineoplastic agents, thereby generating immunogenic cells; and (b) introducing in the subject a cell aggregate which comprises the immunogenic cells and added antigen-presenting cells, thereby inducing an immune response for inhibiting growth of, reducing or eliminating the cell population of the subject.

According to another aspect of the present invention there is provided a method of treating in a subject in need thereof a disease whose pathology involves a pathological cell population of the subject, the method comprising: (a) thermally, mechanically and/or chemically damaging antigen-bearing cells which comprise at least one antigen characterizing the pathological cell population, with the proviso that chemically damaging the antigen-bearing cells is not predominantly effected using one or more antineoplastic agents, thereby generating immunogenic cells; and (b) introducing in the subject a cell aggregate which comprises the immunogenic cells and added antigen-presenting cells, thereby inducing an immune response in the subject against the pathological cell population, thereby treating the disease in the subject.

According to further features in preferred embodiments of the invention described below, the damaging is effected using a cell-damaging treatment selected from the group consisting of freeze-thawing, thermoablation, shock-wave treatment, mechanical disruption, and pressurization.

According to still further features in the described preferred embodiments, the antigen-bearing cells are derived from the cell population.

According to still further features in the described preferred embodiments, the cell aggregate includes a number of the antigen-presenting cells selected from a range of about $1 \times 10^5$ cells to about $2 \times 10^7$ cells.

According to yet another aspect of the present invention, there is provided a therapeutic cell preparation for treating in a subject in need thereof a disease whose pathology involves a pathological cell population of the subject, the cell preparation comprising antigen-presenting cells aggregated with damaged antigen-bearing cells, wherein the damaged antigen-bearing cells comprise at least one antigen characterizing the pathological cell population and further comprise thermally damaged cells, mechanically damaged cells, and/or chemically damaged cells, with the proviso that the chemically damaged cells are not predominantly chemically damaged as a result of being treated with one or more antineoplastic agents.

According to further features in preferred embodiments of the invention described below, the damaged antigen-bearing cells are damaged as a result of being treated with a cell-damaging treatment selected from the group consisting of freeze-thawing, thermoablation, shock-wave treatment, mechanical membrane disruption, pressurization, and chemoablation.

According to still further features in the described preferred embodiments, the cell population comprises cancer cells.

According to still further features in the described preferred embodiments, the cell population comprises tumor cells.

According to still further features in the described preferred embodiments, the cell population comprises cells selected from the group consisting of carcinoma cells, melanoma cells, lung cancer cells, skin cancer cells, sarcoma cells, and liver tumor cells.

According to still further features in the described preferred embodiments, introducing the cell aggregate in the subject comprises administering to the subject a total number of the antigen-presenting cells selected from a range of about $1 \times 10^5$ cells to about $6 \times 10^7$ cells.

According to still further features in the described preferred embodiments, introducing the cell aggregate in the subject comprises administering to the subject a daily dose of the antigen-presenting cells selected from a range of about $1 \times 10^5$ cells per day to about $2 \times 10^7$ cells per day.

According to still further features in the described preferred embodiments, the antigen-bearing cells are included in a tissue of the subject, and introducing the cell aggregate in the subject comprises administering the antigen-presenting cells to the tissue.

According to still further features in the described preferred embodiments, administering the antigen-presenting cells to the tissue comprises administering to the tissue a daily dose of the antigen-presenting cells per weight of the tissue selected from a range of about $2.94 \times 10^6$ cells per gram of the tissue per day to about $1.43 \times 10^9$ cells per gram of the tissue per day.

According to still further features in the described preferred embodiments, administering the antigen-presenting cells to the tissue is effected by administering to the tissue a total dose of the antigen-presenting cells per weight of the tissue selected from a range of about $5.88 \times 10^6$ cells per gram of the tissue to about $4.29 \times 10^9$ cells per gram of the tissue.

According to still further features in the described preferred embodiments, the tissue has a volume selected from a range of about 0.0014 cubic centimeters to about 0.34 cubic centimeters.

According to still further features in the described preferred embodiments, the tissue has a weight selected from a range of about 0.0014 grams to about 0.34 grams.

According to still further features in the described preferred embodiments, a ratio of a weight of the tissue to a weight of the subject is selected from a range of about 0.000056:1 to about 0.0136:1.

According to still further features in the described preferred embodiments, the tissue is a tumor tissue.

According to still further features in the described preferred embodiments, the tissue is a tissue of a tumor which has a potential to metastasize.

According to still further features in the described preferred embodiments, the cell population is a population of cells of a cancer, and the tissue is a tumor tissue of said cancer.

According to still further features in the described preferred embodiments, the cell population is a population of cells of a metastatic cancer, and the tissue is a primary tumor tissue, or a metastatic tumor tissue of the metastatic cancer.

According to a still another aspect of the present invention, there is provided a method of treating a cancer patient having a solid tumor and/or metastasis, the method comprising: (a) thermally, mechanically and/or chemically damaging the solid tumor and/or metastasis in-vivo, with the proviso that the chemically damaging of the solid tumor and/or metastasis is not predominantly effected using one or more antineoplastic agents, thereby generating a damaged site which comprises immunogenic cells; and (b) administering to the subject a therapeutically effective amount of antigen-presenting cells, thereby inducing an immune response in the subject against cells of the solid tumor and/or metastasis, thereby treating the cancer patient.

According to further features in preferred embodiments of the invention described below, the method further comprises: (c) inducing an increase in levels of Th1 cells in the subject.

According to still further features in the described preferred embodiments, administering to the subject the therapeutically effective amount of the antigen-presenting cells comprises administering the antigen-presenting cells to the damaged site.

According to still further features in the described preferred embodiments, the damaging of the solid tumor and/or metastasis is effected using a cell-damaging treatment selected from the group consisting of freeze-thawing, thermoablation, shock-wave treatment, mechanical membrane disruption, pressurization, and chemoablation.

According to still further features in the described preferred embodiments, the cancer patient has a cancer selected from the group consisting of a carcinoma, a melanoma, a lung cancer, a skin cancer, a sarcoma and a liver cancer.

According to still further features in the described preferred embodiments, the solid tumor and/or metastasis is of a cancer selected from the group consisting of a carcinoma, a melanoma, a lung cancer, a skin cancer, a sarcoma and a liver cancer.

According to still further features in the described preferred embodiments, administering to the subject the therapeutically effective amount of the antigen-presenting cells comprises administering to the subject a total dose of the antigen-presenting cells selected from a range of about $1 \times 10^5$ cells to about $6 \times 10^7$ cells.

According to still further features in the described preferred embodiments, administering to the subject the therapeutically effective amount of the antigen-presenting cells comprises administering to the subject a daily dose of the antigen-presenting cells selected from a range of about $1 \times 10^5$ cells per day to about $2 \times 10^7$ cells per day.

According to still further features in the described preferred embodiments, administering to the subject the therapeutically effective amount of the antigen-presenting cells comprises administering to the subject a daily dose of the antigen-presenting cells per weight of the solid tumor and/or metastasis selected from a range of about $2.94 \times 10^6$ cells per gram of the solid tumor and/or metastasis per day to about $1.43 \times 10^9$ cells per gram of the solid tumor and/or metastasis per day.

According to still further features in the described preferred embodiments, administering to the subject the therapeutically effective amount of the antigen-presenting cells comprises administering to the subject a total dose of the antigen-presenting cells per weight of the solid tumor and/or metastasis selected from a range of about $5.88 \times 10^6$ cells per gram of the solid tumor and/or metastasis to about $4.29 \times 10^9$ cells per gram of the solid tumor and/or metastasis.

According to still further features in the described preferred embodiments, the solid tumor and/or metastasis has a volume selected from a range of about 0.0014 cubic centimeters to about 0.34 cubic centimeters.

According to still further features in the described preferred embodiments, the solid tumor and/or metastasis has a weight selected from a range of about 0.0014 grams to about 0.34 grams.

According to still further features in the described preferred embodiments, a ratio of a weight of the solid tumor and/or metastasis to a weight of the subject is selected from a range of about 0.000056:1 to about 0.0136:1.

According to still further features in the described preferred embodiments, the solid tumor has a potential to metastasize.

According to still further features in the described preferred embodiments, the immunogenic cells comprise dying cells and/or dead cells.

According to still further features in the described preferred embodiments, the immunogenic cells comprise necrotic cells and/or apoptotic cells.

According to still further features in the described preferred embodiments, the antigen-presenting cells are capable of displaying at least one antigen-presenting molecule of the subject.

According to still further features in the described preferred embodiments, the antigen-presenting cells are autologous to the subject.

According to still further features in the described preferred embodiments, the antigen-presenting cells are exogenous to the subject.

According to still further features in the described preferred embodiments, the antigen-presenting cells are dendritic cells.

According to still further features in the described preferred embodiments, the antigen-presenting cells are cultured antigen-presenting cells.

According to still further features in the described preferred embodiments, the antigen-presenting cells are immature antigen-presenting cells.

According to still further features in the described preferred embodiments, the one or more antineoplastic agents comprise a mitosis inhibitor, a vinca alkaloid and/or vincristine. The present invention successfully addresses the shortcomings of the presently known configurations by providing a method of using APC vaccination combined with thermal/mechanical/chemical induction of cellular damage for effectively reducing, growth-inhibiting or eliminating in a subject a cell population, such as a pathological population, which is characterized by at least one antigen, with the proviso that the chemical damaging of the antigen-bearing cells is not predominantly effected using one or more antineoplastic agents. Specifically, the present invention provides a method of using dendritic cell vaccination combined with tumor cryoablation for effectively treating metastatic cancer without, or with minimal chemotherapy and/or irradiation treatment.

The present invention successfully addresses the shortcomings of the presently known configurations by teaching that killing or damaging a pathological tissue for disease treatment, such as solid tumor treatment, is optimally achieved via a combination of a cell/tissue-damaging treatment such as cryoablation and in-situ administration of antigen-presenting cells into the pathological tissue, such optimal achievement being relative to either of these treatments alone, or treatment via combined cell/tissue-damaging treatment such as cryoablation and systemic administration of antigen-presenting cells.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1a-b are cytotoxicity assay histograms depicting that treatment of tumor-bearing mice with combined cryoablation/intratumoral dendritic cell injection induces maximal/synergistic and high-level specific anti-tumor cytotoxic capacity in CTLs of the mice. 3LL-D122 carcinoma-bearing C57BL/6 mice were treated twice, with a one-week interval between treatments, as follows: no treatment, cryoablation only (Cryo), intratumoral injection of one million dendritic cells only (DC i.t.), or combination of cryoablation and either in-situ (DC i.t.+Cryo) or intravenous (DC i.v.+Cryo) dendritic cell injection. A negative control group received intratumoral injections of PBS. Ten days following the final treatment, splenocytes of the treated mice were harvested and were restimulated on irradiated and mitomycin C-treated $K^b$39.5 cells for 5 days, and were reacted in a cytotoxicity assay with 5,000 $^{35}$S-methionine-labelled 3LL-D122 target cells (specific targets, FIG. 1a), or B16 melanoma cells (non-specific targets, FIG. 1b), for 5 hours at 37 degrees centigrade. Effector-to-target ratios of 100:1, 50:1, 25:1 are shown. Spontaneous release did not exceed 20 percent of maximal release. Results are representative of three independent experiments. Note the synergistic induction of anti-tumor CTL generation achieved using combined cryoablation and intratumoral dendritic cell injection at a target-to-effector ratio of 25:1 relative to either of these treatments alone.

FIG. 2 is a histogram depicting metastasis development assay results showing that treatment of a spontaneously metastatic primary tumor via combined cryoablation and intratumoral dendritic cell injection completely inhibits metastatic spread. C57BL/6 (8 mice per group) were inoculated intra-foot pad with two-hundred thousand 3LL-D122 cells. Two weeks later, when the tumors reached 3-4 millimeters in diameter, the mice were treated as follows: cryoablation (Cryo) only; intratumoral (DC i.t.) or intraperitoneal (DC i.p.) dendritic cell injection only; or cryoablation in combination with intratumoral (DC i.t. Cryo) or intraperitoneal (DC i.p. Cryo) dendritic cell injection. When tumors reached diameters of 8 mm, a stage corresponding to significant development of pulmonary metastases in untreated mice, the tumor-bearing feet were surgically removed and 23-30 days later, in accordance with the death of the control group, mice were sacrificed and lung weight representing metastatic load was determined. The results are presented as mean lung weight (milligrams) plus/minus standard deviation (SD). The dotted line represents the normal lung weight. Statistical significance was determined by unpaired Welch t-test: p=0.0034,  p=0.0019, * p<0.0001.

DESCRIPTION OF THE PREFERRED EMBODIMENTS

Figure 3:
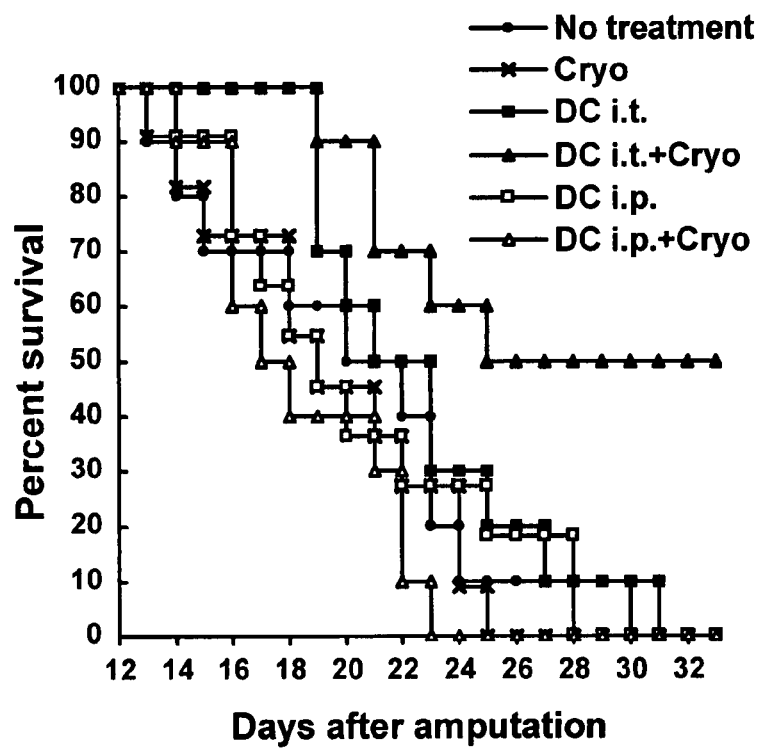
FIG. 3 is a data plot depicting that fifty percent of mice in which lethal metastatic tumors are induced display stable, prolonged survival following treatment via combined cryoablation and intratumoral dendritic cell injection, whereas no mice survive following either treatment only, or following treatment via intraperitoneal dendritic cell injection alone or in combination with cryoablation. Survival of C57BL/6 mice (10-11 mice per group), treated as indicated, was monitored over time following surgical removal of the intra-foot pad implanted primary 3LL-D122 tumors. Percent survival of each treated groups is plotted against time (days) following amputation of tumor-bearing feet. Statistical significance was determined by the log-rank test analyzing survival of mice treated by combined intratumoral dendritic cell injection and cryoablation (DC i.t.+Cryo) in relation to other groups as follows: no treatment (p=0.0092), cryoablation (Cryo; p=0.0042), intratumoral dendritic cell injection (DC i.t.; p=0.0219), intraperitoneal dendritic cell injection (DC i.p.; p=0.0071), and combined intraperitoneal dendritic cell injection and cryoablation (DC i.p.+Cryo; p=0.0011).

The present invention relates to methods of reducing, growth-inhibiting or eliminating a cell population of a subject in need thereof, to methods of treating in a subject in need thereof a disease whose pathology involves a pathological cell population of the subject, to methods of treating a cancer patient having a solid tumor and/or metastasis, to therapeutic cell preparations for treating such diseases, and to methods of obtaining such cell preparations. Specifically, the present invention relates to use of combined antigen-presenting cell (APC) vaccination and localized cell ablation for reducing/growth-inhibiting/eliminating a cell population of a subject, where the cell population is characterized by at least one antigen. Specifically, the present invention further relates to therapeutic cell preparations which comprise immunogenic aggregates of antigen-bearing cells and antigen-presenting cells which are capable of inducing in a subject in need thereof an immune response against a cell population, such as a metastatic cancer cell population, which is specifically associated with at least one antigen. By virtue of enabling reduction/growth-inhibition/elimination of a cell population which is specifically associated with at least one antigen, the method enables treatment of a disease whose pathology involves a such a pathological cell population. Thus, the present invention enables effective treatment of diseases, such as tumors, precancers, cancers, intracellular pathogen-infections, and lymphocyte-mediated autoimmune diseases whose pathologies involve such pathological cell populations, and for which no satisfactory/optimal treatment methods are available. The present invention is particularly suitable for treatment of tumors, such as metastatic/potentially metastatic tumors. The present invention is advantageous over prior art methods of disease-treatment involving combined APC vaccination and cell ablation by virtue of enabling disease treatment using thermal, mechanical and/or chemical cell ablation methods which do not involve use of particularly harmful antineoplastic drugs and/or irradiation.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

No optimal therapy exists for treatment of numerous types of diseases whose pathology involves a pathological cell population characterized by at least one antigen, such as cancers, and in particular lethal, metastatic cancers. While prior art localized cell ablation methods, such as tumor cryoablation, are effective in treating localizable accessible lesions, such as primary tumors, of various types of cancers, such therapy has no systemic therapeutic effect on distant lesions, such as metastatic lesions, and on locally recurrent disease. Therefore, a potentially optimal strategy for treating a metastatic cancer would be to ablate localized accessible lesions using non-radiotherapeutic/non-chemotherapeutic means, in particular using freeze-thawing, in combination with APC vaccination, in particular intratumoral dendritic cell vaccination, to induce systemic immunity to eliminate residual cells/tissues of such lesions, and of distant lesions.

Various methods of treating cancer using combined tumor cryoablation, and APC vaccination have been described by the prior art, as mentioned above.

Such approaches have involved use of hyperthermic treatment/thermoablation or freeze-thawing to induce necrosis of tumor cells; in-vitro exposure of APCs to necrotic tumor cells, or to antigen preparations thereof, to expose the APCs to tumor cell antigens; in-vitro exposure of APCs to exosomes of syncitia of necrotic tumor cells having been genetically modified to express a viral fusogenic protein to expose the APCs to tumor cell antigens; and/or exposure of APCs to antigens of rodent thymoma cells, human monoblastoid leukemia tumor cells, human melanoma cells, or human B-lymphoblastoid leukemia cells.

Various methods of treating cancer using combined tumor ablation, and intratumoral APC vaccination have been described by the prior art, as mentioned above.

Such approaches have involved intratumoral administration of APCs into tumor tissues damaged via antineoplastic agents/chemotherapy or irradiation/radiotherapy.

However, all prior art approaches suffer from various drawbacks, including their being excessively complex/cumbersome to practice, their failing to achieve generation of APCs potentially suitable for cancer treatment, their failing to achieve therapeutic efficacy, and/or, particularly in the case of approaches based upon chemotherapy/radiotherapy, their being associated with particularly harmful side-effects.

Thus, all prior art approaches for treating cancer using combined tumor cryoablation and APC vaccination have failed to provide adequate solutions for treatment of cancer, in particular of metastatic cancer.

While reducing the present invention to practice, treatment of lethal, metastatic cancer via combined tumor cryoablation and intratumoral APC administration, compared to either treatment type alone, was unexpectedly found to result in maximal/synergistic induction of generation of specific anti-tumor cytotoxic T-lymphocytes (CTLs), to uniquely result in essentially complete prevention/elimination of metastasis spread, and to uniquely result in extended survival of any treated subjects, such extended survival being moreover achieved in a large proportion (50 percent) of treated subjects. As such, the present invention enables for the first time use of combined localized cell ablation, particularly cryoablation, and APC vaccination, particularly intratumoral APC vaccination, without use of particularly harmful prior art antineoplastic agents/irradiation, for effective treatment of a subject having a disease, in particular a metastatic/potentially metastatic tumor, whose pathology involves a pathological cell population of the subject, where the pathological cell population is characterized by at least one antigen.

While further reducing the present invention to practice it was uncovered that treatment of tumor-bearing mammals with combined tumor cryoablation and intratumoral dendritic cell administration specifically induces maximal levels of Th1 cells in the subject relative to either treatment alone or to combined tumor cryoablation and intravenous dendritic cell administration.

Thus, the present invention provides a method of inhibiting a growth of, reducing or eliminating a cell population of a subject in need thereof. The method is effected in a first step by thermally, mechanically and/or chemically damaging antigen-bearing cells which comprise at least one antigen characterizing cells of the cell population, with the proviso that the chemically damaging is not predominantly effected using one or more antineoplastic agents, to thereby generate immunogenic cells. In a second step the method is effected by introducing in the subject a cell aggregate which includes the immunogenic cells and added antigen-presenting cells (APCs). It will be appreciated, as described further hereinbelow, that introduction of such an aggregate in the subject will induce an immune response in the subject against the cell population so as to reduce, growth-inhibit or eliminate the cell population.

The method of the present invention can be used to reduce/growth-inhibit/eliminate any cell population of a subject, where the cell population is characterized by at least one antigen, in particular where the cell population specifically includes, or is specifically associated with, an antigen. As such, the method of the present invention can thereby be used to treat in a subject any disease whose pathology involves a pathological cell population which specifically includes an antigen. In particular, as described and illustrated in Example 2 of the Examples section which follows, the method of the present invention can be used for reducing/growth-inhibiting/eliminating such a pathological cell population, namely a lethal, metastatic cancer cell population, in a mammalian subject. As such the method of the present invention can be used for treating a disease, such as a lethal, metastatic cancer in a human subject. As further described hereinbelow, the method of the present invention can further particularly be used, for example, to reduce/growth-inhibit/eliminate pathological cell populations which are specifically associated with antigens, such as populations of pathogen-infected cells, or populations of autoantigen-specific lymphocytes, so as to thereby treat in a human subject an infection by an intracellular pathogen, or an autoantigen-specific autoimmune disease, respectively. Alternately, the method of the present invention can be used to reduce/growth-inhibit/eliminate a cell population which is not inherently pathological, but which specifically includes an antigen, and whose reduction/growth-inhibition/elimination can be used to achieve a desired result, such as a cosmetic modification of the subject.

As used herein, "inhibiting growth of" a cell population refers to preventing or attenuating an increase in the total mass and/or volume of the cell population, and/or to preventing or attenuating an increase in the number of cells of the cell population.

As used herein, "reducing" a cell population refers to reducing the total mass and/or volume of the cell population, and/or to reducing the number of cells of the cell population.

As used herein, an antigen which "characterizes" a cell population of a subject of the present invention (hereinafter "target antigen") refers to an antigen which is substantially included only in the cell population, but not in the other cells of the subject; or which is included in the cell population at substantially higher levels (e.g. at least 50 percent higher levels) than in the other cells of the subject.

As used herein, the term "treating", when relating to a disease of the present invention, refers to preventing onset of the disease; alleviating, attenuating, palliating or eliminating the symptoms of a disease; slowing, reversing or arresting the progression of the disease; or curing the disease.

As used herein, the term "disease" refers to any medical disease, disorder, condition, or syndrome; or to any undesired/abnormal physiological, morphological, cosmetic or physical state/condition of a mammalian subject.

As used herein, the phrase "added APCs" refers to APCs which are administered to the subject, as opposed to APCs, such as natural APCs of the subject which encounter immunogenic cells in-vivo via natural immunophysiological processes.

Preferably, the subject is a homeotherm, more preferably a mammal, and most preferably a human.

According to the teachings of the present invention, damaging the antigen-bearing cells is performed in such a way as to generate immunogenic cells of the present invention which will enable uptake of at least one target antigen included therein by APCs of the present invention, so as to thereby enable the APCs to induce in the subject target-antigen specific immunoreactivity against the cell population to be reduced/growth-inhibited/eliminated (hereinafter "target cell population"). The use of cell-damaging methods to generate immunogenic cells according to the teachings of the present invention is a particular advantage of the presently taught method over the use of prior art radiation-/chemotherapy-based methods, which have the disadvantages of being excessively complex/cumbersome to perform, and of being associated with particularly harmful local/systemic side-effects.

The method of the present invention may be practiced by introducing the cell aggregate in the subject in any of various ways, depending on the application and purpose.

According to a preferred embodiment, the method is employed to reduce/growth-inhibit/eliminate a target cell population of a subject having a tissue which includes antigen-bearing cells of the present invention, preferably a tissue which is predominantly composed of, or most preferably which is essentially formed by, antigen-bearing cells of the present invention. This embodiment particularly relates to reducing/growth-inhibiting/eliminating a pathological cell population of a disease whose pathology involves significant tissue concentrations of such pathological cells. Such diseases, which are well known to one of ordinary skill in the art, include tumors, cancers, precancers and intracellular pathogen infections whose pathology is associated with formation of tissues which include pathological cells.

According to this embodiment, the cell aggregate is introduced in the subject by subjecting an in-vivo tissue of the subject which includes antigen-bearing cells of the present invention to a cell-damaging treatment of the present invention, to thereby generate suitable immunogenic cells in the damaged tissue. Afterwards, APCs of the present invention are administered to the treated/damaged tissue containing the immunogenic cells, thereby introducing in the subject a cell aggregate of the present invention.

Preferably, the APCs are administered to the damaged tissue as described in Example 2 of the Examples section below.

The APCs may be suitably administered to the damaged tissue as a concentrated cell suspension so as to promote aggregation thereof with immunogenic cells thereof. As described in Example 2 of the Examples section below, a cell aggregate of the present invention can be successfully formed by injecting into an in-vivo damaged tissue of the present invention one to two million APCs of the present invention in a volume of 50 microliters, i.e. as a cell suspension of 20 to 40 million cells per milliliter.

Ample guidance for suitably administering APCs to a damaged tissue, such as a damaged tumor tissue, in accordance with the teachings of the present invention is provided in the literature of the art (refer, for example, to: Chen Z. et al., J Gene Med. 2004 Dec. 6; [Epub ahead of print]); Teitz-Tennenbaum S. et al., 2003. Cancer Res. 63:8466-75; Shin JY. et al., 2003. Histol Histopathol. 18:435-47; U.S. Patent Application No. 20040057935 to Yu et al.).

Alternately, according to this embodiment of the method of the present invention, the cell aggregate may be introduced in the subject by removing from the subject a tissue including antigen-bearing cells of the present invention, for example, via standard surgery/biopsy methods, subjecting the tissue to the cell-damaging treatment, and afterwards administering the APCs to the resultant damaged tissue containing immunogenic cells of the present invention, so as to form the cell aggregate ex-vivo. The cell aggregate is then administered to the subject at a suitable anatomical location, thereby introducing the cell aggregate in the subject. Suitable anatomical locations to which the cell aggregate may be administered are described hereinbelow.

When practicing the method according to this embodiment to treat a cancer patient having a metastatic/potentially metastatic cancer, the cell-damaging treatment may be applied to a solid primary tumor tissue, or to a solid metastasis tissue, involved in the pathology of the cancer so as to generate a damaged site which comprises the immunogenic cells. APCs of the present invention are then preferably administered to the damaged site to thereby induce an immune response in the subject against cells of the solid primary tumor tissue or metastasis tissue, to thereby treat the cancer patient. It will be appreciated that by virtue of enabling elicitation of systemic immunoreactivity against cells of a tumor, the method can be used to reduce/growth-inhibit/eliminate a population of metastatic tumor cells when applying the cell-damaging treatment to a primary tumor tissue, and conversely can be used to reduce/growth-inhibit/eliminate a population of primary tumor cells when applying the cell-damaging treatment to a metastatic tumor tissue.

It will be appreciated that a target antigen of the present invention, and factors, such as pro-inflammatory factors, necessary for functionalizing APCs of the present invention may be shed from the damaged site into surrounding tissues, and hence that the method of the present invention according to this embodiment may be effected by administering antigen-presenting cells of the present invention to the damaged site and/or to a target-antigen-containing tissue located adjacent to, and/or surrounding, the damaged site.

According to a further embodiment, the method of the present invention may be employed to reduce/growth-inhibit/eliminate a cell population which does not form a tissue, or which is not included at significant tissue concentrations in the subject. This embodiment particularly relates to treating a disease whose pathology involves, for example, pathological cells located in body fluids. Such diseases include, for example, diseases of circulating hematopoietic cells such as leukemias, lymphocyte-mediated/antigen-specific autoimmune diseases, pathogen infections such as viral infections of circulating hematopoietic cells, as described further hereinbelow.

According to this embodiment, introducing the cell aggregate in the subject may be effected, for example, by harvesting pathological cells from the blood of the subject, subjecting the harvested cells to the cell-damaging treatment in-vitro/ex-vivo, mixing the resultant immunogenic cells with APCs of the present invention within a suitable biocompatible matrix enabling stable aggregation of the cell mixture, and administering the resultant matrix-bound cell aggregate to the subject. Alternately, the immunogenic cells and the APCs may simply be injected, as a mixed, highly/maximally concentrated cell suspension (e.g. 40 million cells per milliliter) in a suitable physiologically balanced carrier, into a suitable anatomical location of the subject enabling stable aggregation of the administered cell suspension.

Physiologically balanced carriers suitable for administering cell suspensions of the present invention to the subject include phosphate-buffered saline (PBS), 9 percent saline, Hank's balanced salt solution (HBSS), and the like.

Harvesting of pathological hematopoietic cells from the blood, such as leukemic cells, pathogen-infected cells or autoantigen-specific lymphocytes is routinely performed in the art, for example using common techniques which exploit specific cell surface marker display by pathological cells, such as leukapheresis, fluorescence activated cell sorting (FACS), magnetic cell sorting (MACS), and the like.

Administration to a mammalian subject of cell aggregates within biocompatible matrices is routinely performed in the art. Examples of suitable biocompatible matrices include, for example, collagen scaffolds, synthetic polymer foams, tissue engineering scaffolds and the like. Ample guidance for using such matrices so as to enable practicing of the method of the present invention is provided in the literature of the art (refer, for example, to: Sachlos E, Czernuszka J T., 2003. Making tissue engineering scaffolds work. Review: the application of solid freeform fabrication technology to the production of tissue engineering scaffolds. Eur Cell Mater. 5:29-39). Such matrices may be suitably administered surgically.

Damaging antigen-bearing cells in-vitro/ex-vivo as described hereinabove enables optimally controlled, homogeneous application of the cell-damaging treatment to antigen-bearing cells which in turn enables optimally reproducible and controllable generation of immunogenic cells. Such in-vitro/in-vivo cell-damaging treatment also has the advantage of minimizing damaging of healthy/bystander tissues when applying the cell-damaging treatment in-vivo in the subject. Administration to the subject of an in-vitro/ex-vivo-formed cell aggregate of the present invention advantageously enables administration of the cell aggregate to an anatomical location of the subject which: (i) is optimal for re-application of the cell-damaging treatment to the cell aggregate; (ii) is optimal for removal of the cell aggregate from the subject; (iii) is optimal for antigen-uptake by the administered APCs; (iv) is optimal for induction of immunoreactivity by the administered APCs; and/or (v) will be minimally/acceptably damaged as a result of inflammation caused by necrotic and immune processes associated with the cell aggregate. A cell aggregate of the present invention formed ex-vivo/in-vitro may be administered to the subject at any one of various suitable anatomical locations, depending on the application and purpose.

A preferred anatomical location for introducing an ex-vivo/in-vitro-formed cell aggregate of the present invention is under the skin (subcutaneously). Administration of the cell aggregate to the subcutaneous anatomical location, by virtue of the natural role of the skin in antigen-uptake by APCs, by virtue of its optimal accessibility to human intervention, and by virtue of its remoteness from vital organs, provides a structural and physiological environment which facilitates: (i) stable aggregation of cells administered thereto; (ii) uptake of target antigens, and consequent induction of target antigen-specific immunoreactivity against a target cell population; (iii) administration/removal of a cell aggregate of the present invention; (iv) in-vivo application of further treatments, such as re-application of cell-damaging treatments of the present invention to an administered cell aggregate of the present invention, and/or (v) avoidance of particularly harmful inflammatory processes, for example those which would be associated in-situ immunotherapy of a tumor located in a vital organ, or other particularly sensitive site of the body where the risk of harmful inflammation should preferably be avoided.

Alternately, the cell aggregate may be advantageously administered to the subject at an anatomical location such as within a secondary lymphoid tissue (e.g. lymph node, spleen, Peyer's patch, etc.), intradermally or intramuscularly. This can be achieved using suitable medical/surgical techniques known to one ordinarily versed in the art. Due to the dense cellular packing of lymphoid tissues, administration of a cell suspension in such an anatomical location is particularly suitable for facilitating stable cellular aggregation thereof. A secondary lymphoid tissue due its natural role in APC-mediated antigen-specific activation of T-lymphocytes, has a physiology which is particularly suitable for enabling reduction/growth-inhibition/elimination of a target cell population according to the teachings of the present invention.

It will be appreciated that the method of the present invention may be advantageously practiced by introducing in the subject any one of various numbers of cell aggregates of the present invention at any one of various numbers and/or types of suitable anatomical locations.

The method of the present invention may be practiced by damaging according to the teachings of the present invention any one of various types of antigen-bearing cells, depending on the application and purpose.

Preferably, the antigen-bearing cells are derived from the target cell population.

The antigen-bearing cells are preferably directly derived from the target cell population, i.e. they are preferably a subset of the cell population. Examples of antigen-bearing cells which are a subset of a target cell population of the present invention include, for example, antigen-bearing cells which are located in-situ in the subject, such as cancer cells located in an in-situ tumor tissue of the subject, or antigen-bearing cells which are a primary isolate of the subject, for example, cells harvested from the subject but which have not been subjected to ex-vivo culturing and expansion. As is described and illustrated in Example 2 of the Examples section below, the method of the present invention can be effectively practiced by damaging according to the teachings of the present invention antigen-bearing cells located in a tissue of the subject, as exemplified by damaging an in-situ tumor tissue of the subject.

It will be appreciated by the ordinarily skilled artisan that a pathological cell population, such as a population of tumor cells, cancer cells, precancer cells, pathogen-infected cells, or autoantigen-specific lymphocytes, generally includes at least one suitable target antigen enabling practicing the method of the present invention. For example, numerous experiments and medical treatments described in the art clearly teach that a cancerous or precancerous target cell population essentially always inherently includes at least one suitable target antigen, for example in the form of a polypeptide which is mutated, or a polypeptide/lipid which is expressed at abnormally high levels, or which is not normally expressed postgestationally. Similarly, an intracellular pathogen-infected target cell population also inherently includes at least one suitable target antigen in the form of a pathogen-encoded polypeptide or lipid; and a population of autoantigen-specific lymphocytes inherently includes a suitable target antigen in the form of an autoantigen-binding antigen receptor, i.e. a B-cell receptor (BCR) or antibody, in the case of B-lymphocytes/plasma cells; or a T-cell receptor (TCR), in the case of T-lymphocytes.

As such, it will be appreciated that the use of antigen-bearing cells which are derived from a target cell population of the present invention is highly suitable for practicing the method of the present invention, as described and illustrated in Example 2 of the Examples section which follows with respect to use of a tumor tissue of a subject as the antigen-bearing cells.

Alternately, the antigen-bearing cells may be indirectly derived from the target cell population, for example, via ex-vivo culturing/expansion of a subset of cells of the target cell population harvested from the subject. Practicing the method of the present invention by damaging according to the teachings of the present invention ex-vivo-expanded antigen-bearing cells may be advantageous in contexts wherein in-situ tissue concentrations of antigen-bearing cells, or the size of harvestable primary isolates of antigen-bearing cells are too low to enable optimal practicing of the present invention.

Culturing and ex-vivo expansion of primary cell isolates harvested from a subject of the present invention, such as primary isolates of human tumor cells, cancer cells, pathogen-infected cells, leukemia cells, and autoantigen-specific lymphocytes, is routinely performed in the art, and ample guidance for practicing such culturing is available in the literature of the art. Such culturing may be suitably performed in-vitro or in-vivo in a host organism. For example, immunodeficient murine hosts, such as SCID or nude mice, are widely employed in the art for growing human tumors, pathogen-infected cells, autoantigen-specific lymphocytes, and the like. When employing cultured antigen-bearing cells to practice the method of the present invention, care may be advantageously taken to practice such culturing so as to retain inclusion/expression of a target antigen in the cultured cells, and to verify such retention following culturing.

Ample guidance for culturing primary isolates of malignant cells of various types is provided in the literature of the art (refer, for example, to: Ethier S P., 1996. Human breast cancer cell lines as models of growth regulation and disease progression. J Mammary Gland Biol Neoplasia. 1:111-21; Katakura Y. et al., 1998. Immortalization by gene transfection. Methods Cell Biol. 57:69-91; Nakanuma Y. et al., 1997. Monolayer and three-dimensional cell culture and living tissue culture of gallbladder epithelium. Microsc Res Tech. 39:71-84; 2004. Isolation and culture of human colon epithelial cells using a modified explant technique employing a non-injurious approach. Methods Mol. Med. 107:237-48; Rosenbaum T. et al., 2000. Long-term culture and characterization of human neurofibroma-derived Schwann cells. J Neurosci Res. 61:524-32; Oie H K. et al., 1996. Cell culture methods for the establishment of the NCI series of lung cancer cell lines. J Cell Biochem Suppl. 24:24-31; Breathnach A S. et al., 1989. Hyperpigmentary disorders—mechanisms of action. Effect of azelaic acid on melanoma and other tumoral cells in culture. Acta Derm Venereol Suppl (Stockh). 143:62-6; Baylin S B. et al., 1983. The spectrum of human lung cancer cells in culture: a potential model for studying molecular determinants of tumor progression and metastasis. Symp Fundam Cancer Res. 36:281-91; Bruserud O. et al., 2001. New strategies in the treatment of acute myelogenous leukemia (AML): in-vitro culture of aml cells—the present use in experimental studies and the possible importance for future therapeutic approaches. Stem Cells. 19:1-11; Kajigaya Y. et al., 1993. [Serum-free culture for leukemia cells]. Hum Cell. 6:49-56; Rovera G. et al., 1987. Proliferation and differentiation of human myelogenous leukemia and preleukemia cells in culture: identification of stimulatory and suppressor growth factors. Haematologica. 72:104-10).

Ample guidance for culturing pathogen-infected cells, such as virally-infected cells, is provided in the literature of the art (refer, for example, to: Wei S. et al., 2000. 93G, a novel sporadic strain of hepatitis E virus in South China isolated by cell culture. J Med. Virol. 61:311-8; Mabit H. et al., 1996. Primary cultured normal human hepatocytes for hepatitis B virus receptor studies. J. Hepatol. 24:403-12; George S L. et al., 2003. Clinical isolates of GB virus type C vary in their ability to persist and replicate in peripheral blood mononuclear cell cultures. Virology. 316:191-201; Lyman W D. et al., 1993. Tissue culture models of HIV-1 infection. Ann N Y Acad Sci. 693:202-12; Benyoucef S. et al., 1998. Combination of whole blood culture and a rapid and sensitive cell assay for the determination of the cytopathogenicity of human immunodeficiency virus type-1 isolates. J Virol Methods. 71:123-31; Japour A J. et al., 1993. Standardized peripheral blood mononuclear cell culture assay for determination of drug susceptibilities of clinical human immunodeficiency virus type 1 isolates. The RV-43 Study Group, the AIDS Clinical Trials Group Virology Committee Resistance Working Group. Antimicrob Agents Chemother. 37:1095-101).

Ample guidance for culturing pathogen-infected cells, such as intracellular bacterium-infected cells, is provided in the literature of the art (refer, for example, to: Angulo A F. et al., 2003. Colistin sulfate as a suitable substitute of thallium acetate in culture media intended for mycoplasma detection and culture. Biologicals. 31:161-3; Taylor-Robinson D., 1976. The use of organ cultures and animal models in the study of *Mycoplasma pneumoniae* infections. Infection. 1976; 4(1 Suppl):4-8; Timenetsky J. et al., 1992. [Identification of mycoplasma by the growth inhibition of samples isolated from cell cultures]. Rev Saude Publica. 26:17-20; Kobakhidze M., 1976. [Sensitivity of *Mycoplasma hominis* cultures isolated from clinical material to certain antibiotics]. Antibiotiki. 21:49-53; Girardi A J. et al., 1965. *Mycoplasma* isolates from primary cell cultures and human diploid cell strains. Proc Soc Exp Biol Med. 120:760-70).

Ample guidance for culturing pathogen-infected cells, such as intracellular fungus-infected cells, is provided in the literature of the art (refer, for example, to: Merkel G J, Phelps C L., 1988. Factors influencing the interaction of *Candida albicans* with fibroblast cell cultures. Infect Immun. 56:792-801; Horvath L L. et al., 2004. Direct comparison of the BACTEC 9240 and BacT/ALERT 3D automated blood culture systems for *Candida* growth detection. J Clin Microbiol. 42:115-8).

Ample guidance for culturing pathogen-infected cells, such as intracellular protozoan-infected cells, is provided in the literature of the art (refer, for example, to: Visvesvara G S, Garcia L S., 2002. Culture of protozoan parasites. Clin Microbiol Rev. 15:327-8; Fields B S. et al., 1990. Virulence of a *Legionella anisa* strain associated with Pontiac fever: an evaluation using protozoan, cell culture, and guinea pig models. Infect Immun. 58:3139-42).

Ample guidance for obtaining primary isolates of autoantigen-specific lymphocytes is provided in the literature of the art (refer, for example, to: Matsumoto Y., 2000. Characterization of T cell receptor (TCR) of organ-specific autoimmune disease-inducing T cells and TCR-based immunotherapy with DNA vaccines. J Neuroimmunol. 110:1-12; Illes Z. et al., 1999. Identification of autoimmune T cells among in-vivo expanded CD25+T cells in multiple sclerosis. J Immunol. 162:1811-7; Shevach E M. et al., 1998. T lymphocyte-mediated control of autoimmunity. Novartis Found Symp. 215: 200-11; Nakashima M. et al., 1996. The role of T cells expressing TcR V beta 13 in autoimmune thyroiditis induced by transfer of mouse thyroglobulin-activated lymphocytes: identification of two common CDR3 motifs. Clin Immunol Immunopathol. 80:204-10; Wang J, Zhu X., 2004. The role of pathogenic B-cell clones in antibody mediated autoimmune disorders. J Dermatol Sci. 36:141-8). Isolated lymphocyte clones, such as autoantigen-specific clones, can easily be expanded via in-vitro culturing according to standard art methods.

Alternately, the method of the present invention may be practiced by damaging according to the teachings of the present invention antigen-bearing cells which are not derived from a target cell population, but which nevertheless include at least one target antigen of the present invention which is specifically included in the target cell population (referred to hereinafter as "heterologous antigen-bearing cells"). It will be appreciated by the ordinarily skilled artisan that even though heterologous antigen-bearing cells are not derived from a target cell population, by virtue of expressing at least one antigen which is specific to the target cell population, introducing in a subject of the present invention a cell aggregate which includes both APCs of the present invention and immunogenic cells derived from heterologous antigen-bearing cells will result in induction of target antigen-specific immunoreactivity against the target cell population.

The use of heterologous antigen-bearing cells may confer various advantages. Heterologous antigen-bearing cells may advantageously include a target antigen at a desired level, such as at an optimally high level, thereby enabling optimally effective uptake of target antigen by the added APCs, and concomitant optimally effective induction of reduction/growth-inhibition/elimination of a target cell population of the present invention. Heterologous antigen-bearing cells may further be advantageously employed in a context wherein in-situ tissue concentrations of antigen-bearing cells, or the numbers of harvestable primary antigen-bearing cells are too low to enable effective practicing of the present invention, and/or wherein culturing of a primary isolate of antigen-bearing cells is suboptimally effective for obtaining sufficient numbers of antigen-bearing cells for practicing the method of the present invention.

Heterologous antigen-bearing cells may be selected expressing a target antigen naturally, or as a result of genetic modification. Suitable human cell lines derived from clinical isolates which naturally express disease-specific target antigens, and suitable human or animal cell lines which have been genetically modified to express any of many different types of clinically relevant disease-specific target antigens exist and are available, for example from commercial suppliers such as the American Tissue Type Collection (ATCC). Alternately, a suitable cell line expressing optimally high levels of a disease-specific target antigen can be established de-novo via genetic modification, according to standard art techniques (for guidance, refer, for example, to the list of art references provided at the start of the Examples section below, in conjunction, where relevant, with the list of disease-specific antigens listed in Table 1). The use of heterologous antigen-bearing cells which are xenogeneic with the subject may advantageously confer the advantage of minimizing the risk of inducing autoimmunity in the subject directed against non-target antigens shared by a subject and allogeneic antigen-bearing cells of a same species. A pathogen-infected cell population can often be used to infect heterologous host cells with the pathogen, where such host cells can be efficiently cultured in-vitro so as to generate suitable heterologous antigen-bearing cells.

Selection or generation of suitable heterologous antigen-bearing cells which include at least one target antigen of a target cell population generally first requires identification of such a target antigen in the cell population. Identification of antigens which are specific to particular pathological cell population of the present invention, such as population of tumor cells, cancer cells, precancer cells, pathogen-infected cells, and/or autoantigen-specific lymphocytes is a routinely practiced for diagnosing, staging and otherwise characterizing a disease whose pathology involves such a pathological cell population.

Antigens which are specifically included in cancer cell populations (which may be referred to as "tumor-associated antigens" in the art), are routinely identified in the course of diagnosing, staging, grading and otherwise characterizing numerous types of malignant diseases in humans. Ample guidance for identifying an antigen which is specifically included in a malignant cell population is provided in the literature of the art (refer, for example, to: Chen Y T. et al. Identification of human tumor antigens by serological expression cloning. In: Rosenberg S A, editor. Principles and practice of the biologic therapy of cancer. 3rd ed. Philadelphia (PA): Lippincott Williams & Wilkins; 2000. pp. 557-70; http://www.cancerimmunity.org/SEREX/). Table 1 below lists some known genes encoding proteins which were identified as tumor associated antigens, and types of tumors which specifically include such antigens. Examples of antigens which are specifically included in melanoma cells include MART-1/MelanA, gp100, tyrosinase, TRP-1, and TRP-2. It will be appreciated that the cancers listed in Table 1 are amenable to treatment via the method of the present invention.

TABLE 1

Human genes encoding antigens specifically included in cancer cell populations

| Gene Symbol | Gene Name | Chromosomal locus | Disease |
| --- | --- | --- | --- |
| ABL1 | v-abl Abelson murine leukemia viral oncogene homolog 1 | 9q34.1 | Leukemia, chronic myeloid |
| ABL2 | v-abl Abelson murine leukemia viral oncogene homolog 2 (arg, Abelson-related gene) | 1q24-q25 | Leukemia, acute myeloid, with eosinophilia |
| AKT2 | v-akt murine thymoma viral oncogene homolog 2 | 19q13.1-q13.2 | Ovarian carcinoma |
| ARHI | ras homolog gene family, member I | 1p31 | Ovarian cancer |
| ARP | | 3p21.1 | Pancreatic cancer |
| AXIN2 | axin 2 (conductin, axil) | 17q23-q24 | Colorectal cancer |
| BAX | BCL2-associated X protein | 19q13.3-q13.4 | Colorectal cancer T-cell acute lymphoblastic leukemia |
| BCPR | homeobox B9 | 17p13.3 | Breast cancer |
| BRCA1 | breast cancer 1, early onset | 17q21 | Breast cancer-1 Ovarian cancer Breast-ovarian cancer |
| BRCA2 | breast cancer 2, early onset | 13q12.3 | Breast cancer 2, early onset Pancreatic cancer |
| BRCA3 | | 11q23 | Breast cancer-3 |
| BRCA4 | | 13q21 | Breast cancer, type 4 |
| BRCAX | | 13q21 | Breast cancer, type 4 |
| BRCD1 | | 13 | Breast cancer, ductal |
| BRCD2 | | 1p36 | Breast cancer, ductal |
| BUB1 | budding uninhibited by benzimidazoles 1 (yeast homolog) | 2q14 | Colorectal cancer with chromosomal instability |
| CDH1 | cadherin 1, type 1, E-cadherin (epithelial) | 16q22.1 | Endometrial carcinoma Ovarian carcinoma Breast cancer, |
| CLD | congenital chloride diarrhea | 7q22-q31.1 | Colon cancer |
| CSF1R | colony stimulating factor 1 receptor, formerly McDonough feline sarcoma viral (v-fms) oncogene homolog | 5q33.2-q33.3 | Myeloid malignancy, predisposition to |
| CTNNB1 | catenin (cadherin-associated protein), beta 1 (88 kD) | 3p22-p21.3 | Colorectal cancer Hepatoblastoma Pilomatricoma |
| DCC | deleted in colorectal carcinoma | 18q21.3 | Colorectal cancer |
| DEK | DEK oncogene (DNA binding) | 6p23 | Leukemia, acute nonlymphocytic |
| DLEC1 | deleted in lung and esophageal cancer 1 | 3p22-p21.3 | Lung cancer Esophageal cancer |
| DMBT1 | deleted in malignant brain tumors 1 | 10q25.3-q26.1 | Glioblastoma multiforme Medulloblastoma |
| DRA | down-regulated in adenoma | 7q22-q31.1 | Colon cancer |
| ELAC2 | elaC (E. coli) homolog 2 | 17p | Prostate cancer, susceptibility to |

TABLE 1-continued

Human genes encoding antigens specifically included in cancer cell populations

| Gene Symbol | Gene Name | Chromosomal locus | Disease |
| --- | --- | --- | --- |
| EP300 | E1A binding protein p300 | 22q13 | Colorectal cancer |
| ESR1 | estrogen receptor 1 | 6q25.1 | Breast cancer |
|  |  |  | Estrogen resistance |
| ETV6 | ets variant gene 6 (TEL oncogene) | 12p13 | Leukemia, acute lymphoblastic |
| FSHR | follicle stimulating hormone receptor | 2p21-p16 | Premature ovarian failure |
|  |  |  | Ovarian sex cord tumors |
| HNPCC7 | 3346 | 15q21.1 | Colorectal cancer, hereditary nonpolyposis, type 7 |
| HPC1 | hereditary prostate cancer 1 | 1q24-q25 | Prostate cancer, susceptibility to |
| HPCX | hereditary prostate cancer, X-linked | Xq27-q28 | Prostate cancer, susceptibility to |
| HRAS | v-Ha-ras Harvey rat sarcoma viral oncogene homolog | 11p15.5 | Bladder cancer |
| HRPT2 | hyperparathyroidism 2 (with jaw tumor) | 1q25-q31 | Hyperparathyroidism-jaw tumor syndrome |
|  |  |  | Hyperparathyroidism, |
| KAI1 | kangai 1 (suppression of tumorigenicity 6, prostate; CD82 antigen (R2 leukocyte antigen, antigen detected by monoclonal and antibody IA4)) | 11p11.2 | Prostate cancer, susceptibility to |
| KIT | v-kit Hardy-Zuckerman 4 feline sarcoma viral oncogene homolog | 4q12 | Mast cell leukemia |
|  |  |  | Mastocytosis with associated |
| KRAS1P | v-Ki-ras1 Kirsten rat sarcoma 1 viral oncogene homolog, processed pseudogene | 12p12.1 | Colorectal adenoma |
|  |  |  | Colorectal cancer |
| KRAS2 | v-Ki-ras2 Kirsten rat sarcoma 2 viral oncogene homolog | 12p12.1 | Colorectal adenoma |
|  |  |  | Colorectal cancer |
| LCFS2 | mitochondrial ribosomal protein L13 | 18q11-q12 | Lynch cancer family syndrome II |
| LCO | liver cancer oncogene | 2q14-q21 | Hepatocellular carcinoma |
| MADH4 | MAD (mothers against decapentaplegic, *Drosophila*) homolog 4 | 18q21.1 | Pancreatic cancer |
| MCC | mutated in colorectal cancers | 5q21 | Colorectal cancer |
| MERTK | c-mer proto-oncogene tyrosine kinase | 2q14.1 | Retinitis pigmentosa, MERTK-related |
| MET | met proto-oncogene (hepatocyte growth factor receptor) | 7q31 | Renal cell carcinoma, papillary, familial and sporadic |
| MGCT |  | 12q22 | Male germ cell tumor |
| MLH1 | mutL (*E. coli*) homolog 1 (colon cancer, nonpolyposis type 2) | 3p21.3 | Colorectal cancer, hereditary nonpolyposis, type 2 |
| MPL | myeloproliferative leukemia virus oncogene | 1p34 | Thrombocytopenia, congenital amegakaryocytic |
| MSH2 | mutS (*E. coli*) homolog 2 (colon cancer, nonpolyposis type 1) | 2p22-p21 | Colorectal cancer, hereditary nonpolyposis, type 1 |
| MSH6 | mutS (*E. coli*) homolog 6 | 2p16 | Cancer susceptibility |
|  |  |  | Endometrial carcinoma |
|  |  |  | Colorectal |
| MTACR1 | multiple tumor-associated chromosome region 1 | 11p15.5 | Wilms tumor, type 2 |
|  |  |  | Adrenocortical carcinoma, hereditary, 202300 |
| MYC | v-myc avian myelocytomatosis viral oncogene homolog | 8q24.12-q24.13 | Burkitt's lymphoma |
| NRAS | neuroblastoma RAS viral (v-ras) oncogene homolog | 1p13.2 | Colorectal cancer |
| PCAP | predisposing for prostate cancer | 1q42.2-q43 | Prostate cancer, susceptibility to |
| PCBC | 3475 | 1p36 | Prostate cancer, susceptibility to |
| PDGFB | platelet-derived growth factor beta polypeptide (simian sarcoma viral (v-sis) oncogene homolog) | 22q12.3-q13.1 | Meningioma, SIS-related |
|  |  |  | Dermatofibrosarcoma protuberans |
| PDGFRL | platelet-derived growth factor receptor-like | 8p22-p21.3 | Hepatocellular cancer |
|  |  |  | Colorectal cancer |
| PGL2 | paraganglioma or familial glomus tumors 2 | 11q13.1 | Paraganglioma, familial nonchromaffin |
| PGL3 | paraganglioma or familial glomus tumors 3 | 1q21 | Paragangliomas, familial nonchromaffin |
| PHB | prohibitin | 17q21 | Breast cancer, sporadic |
| PIK3CA | phosphoinositide-3-kinase, catalytic, alpha polypeptide | 3q26.3 | Ovarian cancer |
| PMS1 | postmeiotic segregation increased (*S. cerevisiae*) 1 | 2q31-q33 | Colorectal cancer, hereditary nonpolyposis, type 3 |
| PMS2 | postmeiotic segregation increased (*S. cerevisiae*) 2 | 7p22 | Turcot syndrome with glioblastoma |
|  |  |  | Colorectal cancer, |

TABLE 1-continued

Human genes encoding antigens specifically included in cancer cell populations

| Gene Symbol | Gene Name | Chromosomal locus | Disease |
|---|---|---|---|
| PPP2R1B | protein phosphatase 2 (formerly 2A), regulatory subunit A (PR 65), beta isoform | 11q22-q24 | Lung cancer |
| PRCA1 | prostate cancer 1 | 1q24-q25 | Prostate cancer, susceptibility to |
| PRKCA | protein kinase C, alpha | 17q22-q23.2 | Pituitary tumor, invasive |
| PTEN | phosphatase and tensin homolog (mutated in multiple advanced cancers 1) | 10q23.3 | Cowden disease Lhermitte-Duclos syndrome |
| PTPN12 | protein tyrosine phosphatase, non-receptor type 12 | 7q11.23 | Colon cancer |
| RAB27A | RAB27A, member RAS oncogene family | 15q21 | Griscelli syndrome |
| RAD51 | RAD51 (S. cerevisiae) homolog (E. coli RecA homolog) | 15q15.1 | Breast cancer, susceptibility to |
| RAD54L | RAD54 (S. cerevisiae)-like | 1p32 | Lymphoma, non-Hodgkin Breast cancer, invasive intraductal |
| RB1 | retinoblastoma 1 (including osteosarcoma) | 13q14.1-q14.2 | Retinoblastoma Osteosarcoma Bladder cancer, |
| RET | ret proto-oncogene (multiple endocrine neoplasia and medullary thyroid carcinoma 1, Hirschsprung disease) | 10q11.2 | Multiple endocrine neoplasia IIA Medullary thyroid |
| RUNX1 | runt-related transcription factor 1 (acute myeloid leukemia 1; aml1 oncogene) | 21q22.3 | Leukemia, acute myeloid Platelet disorder, familial, with |
| SCLC1 | 354 | 3p23-p21 | Small-cell cancer of lung |
| SLC22A1L | solute carrier family 22 (organic cation transporter), member 1-like | 11p15.5 | Breast cancer Rhabdomyosarcoma Lung |
| SLC26A3 | solute carrier family 26, member 3 | 7q22-q31.1 | Colon cancer Chloride diarrhea, congenital, Finnish type |
| SMARCB1 | SWI/SNF related, matrix associated, actin dependent regulator of chromatin, subfamily b, member 1 | 22q11 | Rhabdoid tumors Rhabdoid predisposition syndrome, familial |
| SRC | v-src avian sarcoma (Schmidt-Ruppin A-2) viral oncogene homolog | 20q12-q13 | Colon cancer, advanced |
| SSTR2 | somatostatin receptor 2 | 17q24 | Lung cancer, small cell |
| ST11 | suppression of tumorigenicity 11 (pancreas) | 3p25 | Pancreatic endocrine tumors |
| ST12 | suppression of tumorigenicity 12 (prostate) | 10pter-q11 | Prostate adenocarcinoma |
| ST3 | suppression of tumorigenicity 3 | 11q13 | Cervical carcinoma |
| ST8 | suppression of tumorigenicity 8 (ovarian) | 6q26-q27 | Ovarian cancer, serous |
| TACSTD2 | tumor-associated calcium signal transducer 2 | 1p32-q12 | Corneal dystrophy, gelatinous drop-like |
| TCF7L2 | transcription factor 7-like 2 (T-cell specific, HMG-box) | 10q25.3 | Colorectal cancer |
| TGFBR2 | transforming growth factor, beta receptor II (70-80 kD) | 3p22 | Colon cancer Colorectal cancer, hereditary nonpolyposis, type 6 |
| THPO | thrombopoietin (myeloproliferative leukemia virus oncogene ligand, megakaryocyte growth and development factor) | 3q26.3-q27 | Thrombocythemia, essential |
| TNFRSF10B | tumor necrosis factor receptor superfamily, member 10b | 8p22-p21 | Squamous cell carcinoma, head and neck |
| TNFRSF6 | tumor necrosis factor receptor superfamily, member 6 | 10q24.1 | Autoimmune lymphoproliferative syndrome |
| TOC | tylosis with oesophageal cancer | 17q24 | Tylosis with esophageal cancer |
| TP53 | tumor protein p53 (Li-Fraumeni syndrome) | 17p13.1 | Colorectal cancer Li-Fraumeni syndrome |
| TP73 | tumor protein p73 | 1p36 | Neuroblastoma |
| TSG101 | tumor susceptibility gene 101 | 11p15.2-p15.1 | Breast cancer |
| VMGLOM | venous malformation with glomus cells | 1p22-p21 | Glomus tumors, multiple |
| WT1 | Wilms' tumor 1 | 11p13 | Wilms' tumor, type 1 Denys-Drash syndrome |
| WT2 | Wilms' tumor 2 | 11p15.5 | Wilms' tumor, type 2 Adrenocortical carcinoma, hereditary |

Antigens which are specifically included in pathogen-infected cell populations, are routinely identified in the course of diagnosing, staging, grading and otherwise characterizing numerous types of diseases associated with such cell populations in humans. As such, it will be well within the purview of one of ordinary skill in the art to identify a suitable target antigen in a target cell population so as to enable practicing of the method of the present invention for treating such diseases. Examples of diseases caused by intracellular pathogens include viral infections, intracellular bacterium infections, intracellular fungus infections, intracellular protozoan infections, and the like.

Ample guidance for identifying a suitable target antigen, such as a virus-encoded antigen, which is included in a virally-infected cell population of the present invention is provided in the literature of the art (refer, for example, to: Wilson C C. et al., 2001. Identification and antigenicity of broadly cross-reactive and conserved human immunodeficiency virus type 1-derived helper T-lymphocyte epitopes. J. Virol. 75:4195-207; Kruger S. et al., 2003. Identification of a naturally processed HLA-DR-restricted T-helper epitope in Epstein-Barr virus nuclear antigen type 1. J. Immunother. 26:212-21; Trojan A. et al., 2003. Immune reactivity against a novel HLA-A3-restricted influenza virus peptide identified by predictive algorithms and interferon-gamma quantitative PCR. J. Immunother. 26:41-6; Novitsky V. et al., 2002. Magnitude and frequency of cytotoxic T-lymphocyte responses: identification of immunodominant regions of human immunodeficiency virus type 1 subtype C. J. Virol. 76:10155-68; Sobao Y. et al., 2001. Identification of hepatitis B virus-specific CTL epitopes presented by HLA-A*2402, the most common HLA class I allele in East Asia. J. Hepatol. 34:922-9; Herr W. et al., 1999. Identification of naturally processed and HLA-presented Epstein-Barr virus peptides recognized by CD4(+) or CD8(+) T lymphocytes from human blood. Proc Natl Acad Sci USA. 96:12033-8; Huang Y H. et al., 2004. Identification of novel HLA-A*0201-restricted CD8+ T-cell epitopes on hepatitis delta virus. J Gen Virol. 85:3089-98).

Ample guidance for identifying a suitable target antigen, such as an intracellular bacterium-derived antigen, which is included in an intracellular bacterium-infected cell population of the present invention is provided in the literature of the art (refer, for example, to: Kohler R B., 1986. Antigen detection for the rapid diagnosis of mycoplasma and *Legionella* pneumonia. Diagn Microbiol Infect Dis. 4:47 S-59S; Yogev D. et al., 1993. Variation and genetic control of surface antigen expression in mycoplasmas: the V1p system of *Mycoplasma hyorhinis*. Zentralbl Bakteriol. 278:275-86; Tang P W, Toma S., 1986. Broad-spectrum enzyme-linked immunosorbent assay for detection of *Legionella* soluble antigens. J Clin Microbiol. 24:556-8).

Ample guidance for identifying a suitable target antigen, such as an intracellular fungus-derived antigen, which is included in an intracellular fungus-infected cell population of the present invention is provided in the literature of the art (refer, for example, to: Nisini R. et al., 2001. Antigenic properties and processing requirements of 65-kilodalton mannoprotein, a major antigen target of anti-Candida human T-cell response, as disclosed by specific human T-cell clones. Infect Immun. 69:3728-36; Woo P C. et al., 2002. Detection of cell wall galactomannoprotein Afmp1p in culture supernatants of *Aspergillus fumigatus* and in sera of aspergillosis patients. J Clin Microbiol. 40:4382-7; Casadevall A. et al., 2002. Induced humoral immunity and vaccination against major human fungal pathogens. Curr Opin Microbiol. 5:386-91; Hogan L H. et al., 1996. Virulence factors of medically important fungi. Clin Microbiol Rev. 9:469-88; Kaufman L., 1992. Immunohistologic diagnosis of systemic mycoses: an update. Eur J. Epidemiol. 8:377-82; Li R K, Cutler J E., 1991. A cell surface/plasma membrane antigen of *Candida albicans*. J Gen Microbiol. 137:455-64; Ikeda R. et al., 1982. Antigenic characterization of *Cryptococcus neoformans* serotypes and its application to serotyping of clinical isolates. J Clin Microbiol. 16:22-9).

Ample guidance for identifying a suitable target antigen, such as an intracellular protozoan-derived antigen, which is included in an intracellular protozoan-infected cell population of the present invention is provided in the literature of the art (refer, for example, to: Cooper J A., 1993. Merozoite surface antigen-I of *plasmodium*. Parasitol Today. 9:50-4; Susanto L, Muljono R., 2001. Preparation of *Toxoplasma gondii* RH strain antigen, antigen analysis and antigen detection in sera: a review. Southeast Asian J Trop Med Public Health. 2:195-201;: Luder C G, Seeber F., 2001. *Toxoplasma gondii* and MHC-restricted antigen presentation: on degradation, transport and modulation. Int J. Parasitol. 31:1355-69; Gradoni L., 2001. An update on antileishmanial vaccine candidates and prospects for a canine *Leishmania* vaccine. Vet Parasitol. 100:87-103).

Disease-specific antigens, in the form of autoantigen-specific antigen receptors, which are specifically included in autoantigen-specific lymphocyte populations, are routinely identified in the course of diagnosing, staging, grading and otherwise characterizing numerous types of autoimmune diseases associated with such lymphocyte populations.

Ample guidance for identifying a suitable target antigen, such as an autoantigen-specific T-cell receptor (TCR), which is included in an autoantigen-specific T-lymphocyte population of the present invention is provided in the literature of the art (refer, for example, to: Moss P, Bell J., 1999. T cell receptor usage in autoimmune disease. Springer Semin Immunopathol. 21:5-17; Matsumoto Y., 2000. Characterization of T cell receptor (TCR) of organ-specific autoimmune disease-inducing T cells and TCR-based immunotherapy with DNA vaccines. J. Neuroimmunol. 110:1-12; Nakashima M. et al., 1996. The role of T cells expressing TcR V beta 13 in autoimmune thyroiditis induced by transfer of mouse thyroglobulin-activated lymphocytes: identification of two common CDR3 motifs. Clin Immunol Immunopathol. 80:204-10; Vandenbark A A. et al., 2001. TCR peptide therapy in human autoimmune diseases. Neurochem Res. 26:713-30; Haskins K., 1999. T cell receptor gene usage in autoimmune diabetes. Int Rev Immunol. 18:61-81).

Ample guidance for identifying a suitable target antigen, such as, an autoantigen-specific B-cell receptor (BCR)/antibody, which is included in an autoantigen-specific B-lymphocyte/plasma cell population of the present invention is provided in the literature of the art (refer, for example, to: Wang J, Zhu X., 2004. The role of pathogenic B-cell clones in antibody mediated autoimmune disorders. J Dermatol Sci. 36:141-8;: Link J M, Schroeder H W Jr., 2002. Clues to the etiology of autoimmune diseases through analysis of immunoglobulin genes. Arthritis Res. 4:80-3; Garchon H J., 2003. Genetics of autoimmune myasthenia gravis, a model for antibody-mediated autoimmunity in man. J Autoimmun. 21:105-10; Dorner T, Lipsky P E., 2002. Abnormalities of B cell phenotype, immunoglobulin gene expression and the emergence of autoimmunity in Sjogren's syndrome. Arthritis Res. 4:360-71; Dorner T, Lipsky P E., 2001. Immunoglobulin variable-region gene usage in systemic autoimmune diseases. Arthritis Rheum. 44:2715-27).

The method of the present invention may be practiced by damaging antigen-bearing cells in any of various ways which enable uptake of target antigens included therein by APCs aggregated therewith.

According to the teachings of the present invention, damaging the antigen-bearing cells according to the teachings of the present invention is preferably effected so as to generate immunogenic cells which comprise dead cells and/or dying cells, most preferably so as to generate immunogenic cells which are dying cells. It will be appreciated by the ordinarily skilled artisan that dying cells possess a marked capacity to facilitate uptake of their antigens by APCs, so as to confer upon such APCs the capacity to induce reduction/growth-inhibition/elimination of a population of cells which include such antigens. Preferably, damaging the antigen-bearing cells is effected so as to generate immunogenic cells which comprise apoptotic and/or necrotic cells. Most preferably, damaging the antigen-bearing cells is effected so as to generate immunogenic cells which are necrotic.

Necrosis and apoptosis are distinct cell death processes which are well characterized in the art. Necrosis is a pathological process which is caused by the uncontrolled, progressive degradative action of enzymes that is generally associated with severe cellular damage. Necrosis is characterized by mitochondrial swelling, nuclear flocculation, uncontrolled cell lysis, and ultimately cell death. Apoptosis, on the other hand, is the mechanism responsible for the programmed physiological elimination of cells. It is characterized by distinct morphologic alterations in the cytoplasm and nucleus, chromatin cleavage at regularly spaced sites, and endonucleolytic cleavage of genomic DNA at internucleosomal sites. This mode of cell death serves to regulate tissue development and is the type of cell death induced by T-lymphocytes. As is known in the art, necrotic cells, such as necrotic cancer cells, are particularly efficient at inducing uptake of their antigens by APCs, and thereby of inducing such APCs to induce specific immunity against cells of such a cancer. It is also recognized in the art that APCs have the capacity to take up antigens of apoptotic cells so as to thereby induce immune responses against such cells. Necrotic cells can be identified, by light, fluorescence or electron microscopy techniques, or via staining with trypan blue, whereby the necrotic cells take up the dye and, thus, are stained blue. Necrotic cells can be distinguished via morphological changes including loss of membrane integrity, disintegration of organelles and/or flocculation of chromatin.

Without being bound to a paradigm, the present inventors are of the opinion, in accordance with suggestions put forth in the art (Sauter B. et al., 2000. J Exp Med. 191:423-34), that application of a cell-damaging treatment of the present invention resulting in necrosis of the antigen-bearing cells results in marked release of pro-inflammatory mediators by the necrotic cells, and thereby in particularly effective uptake of antigens by the added APCs, and subsequent induction of target antigen-specific immunoreactivity against a target cell population of the present invention.

It will be appreciated that, due to physical proximity effects, aggregation of the added APCs with immunogenic cells, according to the teachings of the present invention, will facilitate uptake of antigens included in the immunogenic cells by the APCs. Thus, by virtue of being effected by introducing in the subject APCs which are aggregated with antigen-bearing cells which are damaged in such a way as to optimally promote uptake of their antigens by the APCs, the method of the present invention enables particularly efficient uptake of such antigens by particularly large numbers of APCs. This in turn enables induction of particularly effective target antigen-specific immunoreactivity against a target population of the present invention, so as achieve effective reduction/growth-inhibition/elimination of a target cell population of the present invention, as is clearly described and illustrated in Example 2 of the Examples section which follows with respect to a metastatic target cell population.

While any of various types of cell-damaging treatments of the present invention may be employed to generate suitable immunogenic cells, the cell-damaging treatment employed is preferably freeze-thawing.

Freeze-thawing of cells so as to induce cellular damage therein, particularly resulting in cellular necrosis, may be alternatively referred to in the art as cryotreatment, cryotherapy, cryoablation, etc, and may be performed in any one of various ways, depending on the application and purpose. In cases where antigen-bearing cells of the present invention are located cutaneously or subcutaneously in a tissue of the subject, the freeze-thawing may be suitably performed as described in Example 2 of the Examples section which follows, namely by contacting the tissue with a metal instrument, such as a forceps, pre-chilled in liquid nitrogen (which under typical ambient conditions will be at its boiling temperature of minus 196 degrees centigrade) until freezing of the tissues is achieved, and subsequently allowing the tissues to thaw. An ex-vivo tissue containing antigen-bearing cells of the present invention, or an ex-vivo suspension of antigen-bearing cells of the present invention may be suitably freeze-thawed by immersing a recipient containing the antigen-bearing cells in liquid nitrogen, and subsequently allowing the cells to thaw at ambient temperature.

Alternately, in cases where the antigen-bearing cells are located in-vivo in a tissue which is in a significantly less accessible anatomical location than an intradermal or subcutaneous location, the freeze-thawing may be suitably performed using standard catheter cryoablation techniques. Catheter cryoablation of tissues in-vivo is routinely practiced in the art, for example, in the context of treatment of hepatocellular carcinoma tumors, renal tumors, prostate tumors, and colorectal tumors (refer, for example, to: Han K R, Belldegrun A S., 2004. Third-generation cryosurgery for primary and recurrent prostate cancer. BJU Int. 93:14-8; Johnson D B and Nakada S Y., 2003. Cryoablation of renal and prostate tumors. J Endourol 17:627-32; Adam R. et al., 2004. Surg Clin North Am. 84:659-71). Typically, catheter cryoablation of a tissue, such as of a tumor, is performed by contacting the tissue with a closed circuit cryoprobe containing a chilled or liquefied gas, such as chilled argon gas (De La Taille A. et al., 2000. BJU Int. 85:281-6) or liquid nitrogen. The procedure is preferably performed, where applicable, such as in prostatic cryoablation, in conjunction with real-time ultrasound monitoring of probe placement and freezing (Onik G. et al., 1988. Radiology 168:629-31), and with use of a warming catheter (Saliken J C. et al., 2002. Urology 60:26-33).

It will be appreciated that freezing of cells, especially rapid freezing thereof, induces formation of ice-crystals therein which mechanically damages intracellular and membranal structures thereof such that after subsequent thawing the cells undergo processes such as intracellular dehydration and pH changes which lead to necrosis. Freeze-thawing of a vascularized tissue induces characteristic types of cell/tissue damage such as ischemia via vascular injury associated with vascular hyperpermeability, osmotic swelling, platelet aggregation and microthrombosis consequent to endothelial damage. Parameters modulating the efficiency of cell damage by freeze-thawing include cooling velocity, temperature nadir, freezing duration, thawing velocity, the number of freeze-thaw cycles, and proximity of large blood vessels which may act as heat sinks.

While the use of liquid nitrogen is highly convenient and effective for rapidly freezing cells/tissues so as to induce necrosis therein after thawing, it will be further appreciated that substantially less cold freezing temperatures than those of liquid nitrogen can be used to suitably freeze-thaw antigen-bearing cells of the present invention. Thus, antigen-bearing cells of the present invention may be freeze-thawed, for example using a freezing temperature of minus 2 degrees centigrade or lower. Antigen-bearing cells of the present invention may be conveniently and suitably frozen in the context of freeze-thawing by placement in a standard storage freezer, which typically may have a temperature ranging from approximately minus 20 degrees centigrade to about approximately 85 degrees centigrade. Alternately, antigen-bearing cells of the present invention may be conveniently and suitably frozen in the context of freeze-thawing by immersing a recipient containing such cells in an ethanol-frozen carbon dioxide slush (commonly referred to as an "ethanol-dry ice bath"), which has a temperature of approximately minus 72 degrees centigrade. A suitable standard freezing modality to achieve efficient tumor cell/tissue killing is freezing the cell/tissue at minus 40 degrees centigrade for 3 minutes (Shinohara K. et al., 1996. J. Urol. 156: 115-20; discussion 120-1; Hoffmann N E, Bischof J C., 2002. The cryobiology of cryosurgical injury. Urology. 60:40-9; Han K R, Belldegrun A S., 2004. Third-generation cryosurgery for primary and recurrent prostate cancer. BJU Int. 93:14-8).

Cryoablation/freeze-thawing is a particularly advantageous method of inducing therapeutic cell damaging relative to all other cell-damaging methods. For example, comparative studies have shown that cryoablation of a tissue such as renal parenchyma is superior to other cell-damaging methods such as microwave thermoablation, radiofrequency energy and chemoablation by ethanol, hypertonic saline and acetic acid gels, in terms of reproducibility, consistency in size and shape, and the ability to monitor by ultrasound (Rehman J. et al., 2004. J. Endourol. 18:83-104). Cryoablation/freeze-thawing is clearly advantageous for inducing therapeutic cell damaging over use of irradiation/radiotherapy or antineoplastic agents/chemotherapy which are associated with particularly harmful local/systemic side-effects, and will tend to damage/modify molecular structures required for successful antigen-uptake by APCs and consequent induction of antigen-specific immunoreactivity.

As described in Example 2 of the Examples section below, while reducing the present invention to practice, freeze-thawing of antigen-bearing cells according to the teachings of the present invention achieved for the first time effective treatment of metastatic cancer relative to all prior art methods of treating cancer based on freeze-thawing.

Alternately, suitable cell-damaging treatments for generating immunogenic cells of the present invention include thermal treatments such as thermoablation; mechanical treatments such as shock-wave treatment, mechanical membrane disruption, and pressurization; and chemical treatments such as ethanol ablation, hypertonic saline ablation and acetic acid gel ablation.

The art teaches that such treatments can be used to induce cell damage, in particular cellular necrosis, and one of ordinary skill in the art will possess the necessary expertise for utilizing such cell-damaging treatments for practicing the method of the present invention.

Examples of suitable thermoablative/hyperthermic treatments include, radiofrequency thermoablation, microwave cryoablation, ultrasound thermoablation, hot-water balloon thermoablation, and laser thermoablation. Ample guidance for using thermoablation to induce cell damage, such as tumor cell necrosis, so as to enable practicing of the method of the present invention, for example to treat metastatic cancer, is provided in the literature of the art (refer, for example, to: Sandonato L. et al. 2004. [Radiofrequency thermoablation in the treatment of primary and secondary liver tumours]. Chir Ital. 56:117-26; Rehman J. et al. 2004. Needle-based ablation of renal parenchyma using microwave, cryoablation, impedance- and temperature-based monopolar and bipolar radiofrequency, and liquid and gel chemoablation: laboratory studies and review of the literature. J. Endourol. 18:83-104; Kohrmann K U. et al., 2002. [Control Parameters for High-Intensity Focused Ultrasound (HIFU) for Tissue Ablation in the Ex-vivo Kidney]. Aktuelle Urol. 33:58-63; Jung E M. et al. 2003. [Contrast-enhanced ultrasound with Optison in percutaneous thermoablation of liver tumors]. Rofo. 175:1403-12; Lupo L. et al. 2003. [Anatomical hepatic resection using radiofrequency thermoablation in the treatment of primary or secondary liver tumors]. Tumori. 89(4 Suppl):105-6; Gasparini D. et al., 2002. Combined treatment, TACE and RF ablation, in HCC: preliminary results. Radiol Med (Torino). 104:412-20; Pichler L. et al., 2002. [Radiofrequency-thermoablation in malignant liver disease]. Rofo. 174:1369-74; Kohrmann K U. et al., 2002. Technical characterization of an ultrasound source for noninvasive thermoablation by high-intensity focused ultrasound. BJU Int. 90:248-52; Elias D. et al., 2002. Percutaneous radiofrequency thermoablation as an alternative to surgery for treatment of liver tumour recurrence after hepatectomy. Br J. Surg. 89:752-6; Corica F A. et al., 2000. Transurethral hot-water balloon thermoablation for benign prostatic hyperplasia: patient tolerance and pathologic findings. Urology. 56:76-80; de Jode M G. et al., 1999. MR-guided laser thermoablation of inoperable renal tumors in an open-configuration interventional MR scanner: preliminary clinical experience in three cases. J Magn Reson Imaging. 10:545-9; Larson T R. et al., 1996. Temperature-correlated histopathologic changes following microwave thermoablation of obstructive tissue in patients with benign prostatic hyperplasia. Urology. 47:463-9).

Examples of shock-wave treatments used to damage cells, such as tumor cells, include shock-wave induced cavitation, high energy shock-wave treatment, underwater shock-wave treatment, and the like. Ample guidance for using shock-wave treatment to induce cell damage, such as cancer cell necrosis, so as to enable practicing of the method of the present invention, for example to treat cancer, is provided in the literature of the art (refer, for example, to: Huber P E, Debus J., 2001. Tumor cytotoxicity in-vivo and radical formation in-vitro depend on the shock wave-induced cavitation dose. Radiat Res. 156:301-9; Hoshi S. et al., 1995. High-energy underwater shock wave treatment for internal iliac muscle metastasis of prostatic cancer: a first clinical trial. Jpn J Cancer Res. 86:424-8; Yao C Z. et al., 1994. Cytocidal effect of high energy shock wave on tumour cells enhanced with larger dose and multiple exposures. Surg Oncol. 3:229-35; Darzi A. et al., 1993. High-energy shock waves pyrotherapy. A new concept in extracorporeal tumour therapy. Surg Oncol. 2:197-203).

Examples of mechanical membrane disruption treatments used to damage cells, for example, so as to induce necrosis of such cells, include any of various methods involving contacting cells with a solid object in such a way as to disrupt their cytoplasmic membranes, for example via shearing, tearing, puncturing, shredding, abrasion and/or laceration of the cell membranes. Examples of techniques which can be used to suitably mechanically disrupt cell membranes include freeze-thawing (wherein ice-crystals cause mechanical membrane disruption), particle bombardment (also referred to in the art as microparticle bombardment, particle gun bombardment, microprojectile bombardment, etc.), and cell/tissue shearing using a teflon homogenizer, such as a Dounce homogenizer, and the like. Ample guidance for using particle bombardment to induce cell damage, such as necrotic cell damage, so as to enable practicing of the present invention is provided in the literature of the art (refer, for example, to: Steele K E. et al., 2001. Cutaneous DNA vaccination against Ebola virus by particle bombardment: histopathology and alteration of CD3-positive dendritic epidermal cells. Vet Pathol. 38:203-15).

Examples of pressurization treatments, include hydrostatic pressurization treatments, and mechanical pressurization treatments. Hydrostatic pressurization treatments are typically applied to cells/tissues in-vitro. Ample guidance for using hydrostatic pressurization to induce cell damage, such as in-vitro/ex-vivo cancer cell necrosis induction, so as to enable practicing of the present invention, for example to treat cancer, is provided in the literature of the art (refer, for example, to: Korn A. et al., 2004. High hydrostatic pressure inactivated human tumour cells preserve their immunogenicity. Cell Mol Biol (Noisy-1e-grand). 50:469-77; Glashan R W., 1975. A critical review of the management of bladder neoplasia using a modified form of Helmstein's pressure therapy. Br J. Urol. 47:57-66; Diehl P. et al., 2003. Induction of tumor cell death by high hydrostatic pressure as a novel supporting technique in orthopedic surgery. Oncol Rep. 10:1851-5; Frey B. et al., 2004. Hydrostatic pressure induced death of mammalian cells engages pathways related to apoptosis or necrosis. Cell Mol Biol (Noisy-le-grand). 50:459-67).

Mechanical pressurization treatments, which typically consist of applying pressure to a tissue/cells between two solid surfaces (i.e. "crushing") may be effected either in-vivo or in-vitro. Ample guidance for using mechanical pressurization treatments to induce cell damage, such as cell necrosis, so as to enable practicing of the present invention is provided in the literature of the art (refer, for example, to: Stadler I. et al., 2004. Development of a simple, noninvasive, clinically relevant model of pressure ulcers in the mouse. J Invest Surg. 17:221-7; Peirce S M. et al., 2000. Ischemia-reperfusion injury in chronic pressure ulcer formation: a skin model in the rat. Wound Repair Regen. 8:68-76; Kokate J Y. et al., 1995. Temperature-modulated pressure ulcers: a porcine model. Arch Phys Med Rehabil. 76:666-73).

Suitable chemical cell-damaging treatments for generating immunogenic cells according to the method of the present invention include ethanol ablation, hypertonic saline and acetic acid gel ablation. Such methods are routinely employed in the art, for example for inducing cellular damage, such as necrosis, of cells such as tumor cells. Ample guidance for practicing such methods for suitably damaging cells according to the teachings of the present invention is provided in the literature of the art (refer, for example, to Rehman J. et al., 2004. J. Endourol. 18:83-104).

As described hereinabove, chemically damaging the antigen-bearing cells according to the method of the present invention is effected with the proviso that the cell-damaging is not predominantly effected using one or more antineoplastic agents.

According to the teachings of the present invention, the antineoplastic agent is any substance which selectively kills and/or growth-inhibits dividing cells, in particular a drug which may be administered systemically to a cancer patient for selectively killing and/or growth-inhibiting cancer cells of the patient. Antineoplastic agents according to the present invention are well known and characterized in the art (refer, for example, to Palumbo M., 2004. Curr Med Chem Anti-Canc Agents. 4:425-7), wherein they may also be referred to as antineoplastic drugs, chemotherapeutic agents or drugs, or anticancer agents or drugs.

In particular, according to the teachings of the present invention, the method of the present invention is practiced using a cell-damaging method to generate immunogenic cells which is not predominantly effected, more preferably which does not comprise, using one or more antineoplastic agents comprising vincristine, more particularly using one or more antineoplastic agents comprising a plant alkaloid, and most particularly using one or more antineoplastic agents comprising a mitosis inhibitor.

Antineoplastic agents comprise any of various agents employed in the systemic treatment of malignancies, including, for example, DNA alkylating agents, DNA repair inhibitors, DNA synthesis inhibitors, nitrosoureas, antimetabolites, RNA synthesis inhibitors, or antitumor antibiotics.

Alkylating agents, such as cyclophosphamide, exert cytotoxic activity by directly attacking DNA. Nitrosoureas, such as lomustine (CCNU) and carmustine (BCNU), act similarly to alkylating agents and also inhibit changes necessary for DNA repair. Antimetabolites, such as 5-fluorouracil (5FU) and 6-mercaptopurine, block cell growth, typically by interfering with DNA synthesis during the "S" phase of the cell cycle by halting normal development and reproduction once ingested into the cell. Antitumor antibiotics doxorubicin (adriamycin), mitomycin-C, and bleomycin are a varied category of compounds. They generally function by binding DNA and prevention of RNA synthesis. Plant alkaloids, such as vinca alkaloids, such as vincristine and vinblastine, are derived from plants and act by specifically blocking cell division during mitosis.

The cell-damaging treatment of the present invention may be repeatedly applied to a cell aggregate of the present invention to achieve reduction/growth-inhibition/elimination of a target cell population of the present invention, as described further hereinbelow and in Example 2 of the Examples section which follows.

The method of the present invention may be practiced by introducing in the subject a cell aggregate of the present invention which includes any of various types of APCs. For example, the APCs may be capable of displaying any of various combinations of antigen-presenting molecules, may be any one of various APC cell types, may be at any of various maturation stages, may be derived from any of various organismal sources, and/or may be obtained according to any of various methods.

Preferably, the method of the present invention is practiced using APCs which are capable of displaying at least one, and more preferably a maximal number of, antigen-presenting molecules of the subject. Most preferably, the APCs are derived from the subject (autologous APCs).

Antigen-presenting molecules are a family of molecules including numerous allelic variants each of which being capable of "presenting" a distinct category of intracellularly processed antigen in the form of a cell surface-displayed complex (hereinafter referred to "antigen-presenting complex"). Functionally important antigen-presenting molecules include major histocompatibility complex (MHC) molecules, such as MHC class I or II molecules, which present peptide antigens; and CD1 molecules, which present lipid antigens. During activation of T-lymphocyte-mediated immunity, naïve antigen-specific T-lymphocytes become activated in secondary lymphoid tissues via specific binding of their clonotypic TCR to a complex of an antigen-presenting molecule and a disease-specific antigen displayed at the surface of an activated APC having taken up such an antigen. Such activated T-lymphocytes then exit the lymphoid organ and are stimulated via their TCRs to exert their effector functions against a pathological cell which displays the same antigen-presenting complex with which they were activated.

Autologous APCs are inherently capable of displaying all or a maximal number of the antigen-presenting molecules of the subject, and therefore will be capable of presenting an optimally broad range of different target antigens of a target cell population of the present invention to lymphocytes of the subject, and will thereby be optimally capable of inducing target antigen-specific immunoreactivity against the target cell population. It will be appreciated, in accordance with general art knowledge, that the broad diversity of potential target antigens which can be presented by the various antigen-presenting molecules of a mammalian subject, and the broad diversity of suitable target antigens which is included in a typical pathological target cell population of the present invention ensures that there will generally exist in such a context at least one combination of such a target antigen and such an antigen-presenting molecule which will be capable of forming an antigen-presenting complex enabling induction of target-antigen immunoreactivity against the target cell population, thereby enabling the method of the present invention.

As is described and illustrated in Example 2 of the Examples section below, the present invention may be effectively practiced using autologous APCs, as exemplified in the context of successful treatment of a lethal, metastatic cancer in a mammal.

Nevertheless, the method of the present invention may be practiced using APCs which are not derived from the subject (exogenous APCs), so long as such APCs are capable of displaying at least one antigen-presenting molecule of the subject. Exogenous APCs may be advantageously selected or generated, for example, capable of displaying desired levels of suitable antigen-presenting molecules of the subject to thereby enable optimally effective priming of T-lymphocytes of the subject, so as to thereby induce optimally effective target antigen-specific immunoreactivity against a target cell population. It will be well within the purview of one of ordinary skill in the art to select, for example from allogeneic sources, or to generate, for example via genetic modification of antigen-presenting cells of the subject or from non-syngeneic sources, antigen-presenting cells capable of expressing desired levels of specific antigen-presenting molecules. Ample guidance for selecting or generating such APCs is provided in the literature of the art (for example, refer to: Altmann D M. et al., 1989. Cotransfection of ICAM-1 and HLA-DR reconstitutes human antigen-presenting cell function in mouse L cells. Nature. 338:512-4; Janitz M. et al., 1997. Polymorphic MHC class II promoters exhibit distinct expression pattern in various antigen-presenting cell lines. Tissue Antigens. 49:99-106).

In order to select exogenous APCs which are capable of displaying at least one antigen-presenting molecule of the subject, particularly in cases wherein the APCs are not capable of displaying all of the antigen-presenting molecules of the subject, it may be necessary to identify a suitable antigen-presenting molecule of the subject. It will be well within the purview of one ordinarily versed in the art to perform such identification since typing of antigen-presenting molecules, such as MHC alleles, in humans is very widely practiced in the art, for example in the context of allogeneic transplantation donor-recipient matching. Furthermore, it may be advantageous to select an exogenous APC which is capable of displaying an antigen-presenting molecule of the subject which is specifically capable of displaying a relevant target antigen. This is particularly relevant in cases wherein the immunogenic antigen-bearing cells employed are likely to express only a subset of the potentially suitable target antigens included in a target cell population, such as in the case of a subject-heterologous antigen-bearing cell genetically modified to express a single relevant target antigen. Ample guidance for identifying antigens and antigen-presenting molecules which can form a functional antigen-presenting complex is available in the literature of the art, for example for MHC class I molecules (refer, for example, to: Bianco A. et al., 1998. J Pept Sci. 4:471; Fairchild P J., 1998. J Pept Sci. 4:182; Falk K. and Rotzschke O., 1993. Semin Immunol. 5:81; Rammensee H G., 1995. Curr Opin Immunol. 7:85; and Hobohm U. and Meyerhans A., 1993. Eur J. Immunol. 23:1271), or for MHC class II molecules (refer, for example, to: Fairchild P J., 1998. J Pept Sci. 4:182; Rammensee H G., 1995. Curr Opin Immunol. 7:85; Sinigaglia F. and Hammer J., 1994. APMIS. 102:241; and Hobohm U. and Meyerhans A., 1993. Eur J. Immunol. 23:1271). Additional guidance for suitably genetically modifying APCs is provided hereinbelow.

Preferably, the method of the present invention is practiced by introducing in the subject a cell aggregate which includes APCs that are professional APCs, more preferably which are dendritic cells. Alternately, the APCs employed may be macrophages, monocytes, B-lymphocytes, and the like.

The APCs employed to practice the method of the present invention may be at any of various stages of maturity, depending on the application and purpose.

Preferably, the APCs are immature APCs. In accordance with art knowledge immature rather than mature dendritic cells are particularly efficient at antigen ingestion and processing (Figdor C G. et al., 2004. Nat. Med. 10:475-80). Furthermore, antigens of dying cells, which is the preferred condition of the antigen-bearing cells employed to practice the method of the present invention, are captured fivefold better by immature than by mature dendritic cells (Sauter B. et al., 2000. J Exp Med. 191:423-34). Without being bound to a paradigm, the present inventors are of the opinion that immature dendritic cells are particularly efficiently induced to mature, and to consequently induce antigen-specific systemic immunity, when exposed to dying antigen-bearing cells, in particular necrotic cells.

Suitable dendritic cells may be obtained using any of various commonly practiced art techniques. In general, identification of dendritic cells by surface phenotyping may be accomplished by simply demonstrating a high level of MHC class II or a costimulatory molecule such as CD80 and the absence of lineage markers, such as CD3 (T cell), CD14 (monocyte), CD19 (B cell), CD56 (natural killer cell) and CD66b (granulocyte). Dendritic cells also may express a variety of adhesion molecules including CD11a (LFA-1), CD11c, CD50 (ICAM-2), CD54 (ICAM-1), CD58 (LFA-3), and CD102 (ICAM-3). Immature human dendritic cells typically display low surface levels of the surface marker MHC class II, are negative for the surface marker CD83, do not have a stellate shape, are plastic-adherent, and display active endocytosis. Immature dendritic cells also tend to express B7-2 (CD86) but not B7-1 (CD80). In contrast to, immature dendritic cells, mature dendritic cells generally specifically display CD83 (also stains activated B-cells; Lechmann M. et al., 2002. Trends Immunol. 23:273-5), CMRF-44 (also stains macrophages and monocytes), high levels of MHC class II; have a stellate shape, are plastic non-adherent, and do not display active endocytosis. Activated mature APCs generally display T-lymphocyte co-stimulatory molecules, such as B7-1 (CD80), B7-2 (CD86), and CD40, and have the capacity to secrete IL-12, and to stimulate mixed lymphocyte responses (MLR).

The method of the present invention may be practiced by introducing in the subject a cell aggregate which includes primary APCs and/or cultured APCs Culturing of APCs may be advantageously employed in contexts wherein large numbers of primary APCs are difficult to obtain, such as when using APCs derived from a mammalian subject, which will generally have low tissue concentrations of APCs. Culturing of the APCs advantageously enables generation of APCs under optimally controlled and reproducible conditions, and hence generation of APCs having a desired, and optimally uniform phenotype.

As is described and illustrated in Example 2 of the Examples section below, the method of the present invention may be effectively practiced using cultured APCs derived from a mammalian subject, as successfully exemplified in the context of treatment of lethal, metastatic cancer in the subject.

The APCs may be suitably harvested from a mammal and cultured according to the teachings of protocol described in Example 2 of the Examples section which follows. Alternately, harvesting, and/or culturing of human APCs so as to thereby obtain suitable APCs for practicing the method of the present invention may be performed using any of various techniques routinely practiced in the art.

Thus, the present invention provides a therapeutic cell preparation, and method of obtaining same, for treating in a subject in need thereof a disease whose pathology involves a pathological cell population of the subject, where the cell preparation comprises antigen-presenting cells of the present invention aggregated with damaged antigen-bearing cells of the present invention.

Ample guidance for obtaining suitable APCs for practicing the method of the present invention, such as those described hereinabove, is available in the literature of the art (refer, for example, to: Wilson H L. et al., 2000. Identification of progenitor cells in long-term spleen stromal cultures that produce immature dendritic cells. Proc Natl Acad Sci USA. 97:4784-9; Seager Danciger J. et al., 2004. Method for large scale isolation, culture and cryopreservation of human monocytes suitable for chemotaxis, cellular adhesion assays, macrophage and dendritic cell differentiation. J Immunol Methods. 288:123-34; Celluzzi C M, Welbon C., 2003. Dendritic cell culture: a simple closed culture system using ficoll, monocytes, and a table-top centrifuge. J Hematother Stem Cell Res. 12:575-85; Suri R M, Austyn J M., 1988. Bacterial lipopolysaccharide contamination of commercial collagen preparations may mediate dendritic cell maturation in culture. J Immunol Methods. 214:149-63; Bartz H. et al., 2003. Large-scale isolation of immature dendritic cells with features of Langerhans cells by sorting CD34+ cord blood stem cells cultured in the presence of TGF-beta1 for cutaneous leukocyte antigen (CLA). J Immunol Methods. 275:137-48; Syme R., Gluck S., 2001. Generation of dendritic cells: role of cytokines and potential clinical applications. Transfusion and Apheresis Science 24:117-124; Ni K, O'Neill H C., 2000. Improved FACS analysis confirms generation of immature dendritic cells in long-term stromal-dependent spleen cultures. Immunol Cell Biol. 78:196-204; U.S. Patent Application No. 20040057935; and U.S. Pat. Nos. 5,851,756, 5,994,126, 6,274,378 and 6,485,483).

As a further alternative, suitable cultured immortalized dendritic cell lines may be employed to practice the treatment method of the present invention.

Immortalized human dendritic cell lines suitable for practicing the method of the present invention are routinely cultured in the art (refer, for example, to: Park S M. et al., 2003. Functional effects of TNF-alpha on a human follicular dendritic cell line: persistent NF-kappa B activation and sensitization for Fas-mediated apoptosis. J. Immunol. 171:3955-62; Nagasaki M. et al., 2000. A human B-lineage dendritic cell line, HBM-noda and its potential role in human T-cell leukemia/lymphoma virus type I infection. Pathol Int. 50:280-90).

The APCs employed to practice the method of the present invention may be advantageously treated with factors or cytokines, such as tumor necrosis factor (TNF)-alpha, which promote maturation of APCs such as dendritic cells and concomitant induction of immunoreactivity against a target cell population by such antigen-presenting cells. Ample guidance for culturing dendritic cells such factors is provided in the literature of the art (refer, for example to: Park S M. et al., 2003. Functional effects of TNF-alpha on a human follicular dendritic cell line: persistent NF-kappa B activation and sensitization for Fas-mediated apoptosis. J. Immunol. 171:3955-62; McIlroy D, Gregoire M., 2003. Cancer Immunol Immunother. 52:583-91; Adams M. et al., 2003. Dendritic cell (DC) based therapy for cervical cancer: use of DC pulsed with tumour lysate and matured with a novel synthetic clinically non-toxic double stranded RNA analogue poly [I]:poly [C(12)U] (Ampligen R). Vaccine. 21:787-90; Zou G M, Tam Y K., 2002. Cytokines in the generation and maturation of dendritic cells: recent advances. Eur Cytokine Netw. 13:186-99).

The APCs employed to practice the method of the present invention may be advantageously genetically modified to express growth factors, survival factors and/or factors enhancing induction of APC-mediated immunity. Ample guidance for thusly genetically modifying APCs is provided in the literature of the art (refer, for example, to Jilek S. et al., 2004. Transfection of a mouse dendritic cell line by plasmid DNA-loaded PLGA microparticles in-vitro. Eur J Pharm Biopharm. 58:491-9; Cisco R M. et al., 2004. Induction of human dendritic cell maturation using transfection with RNA encoding a dominant positive toll-like receptor 4. J Immunol. 172:7162-8; Ueno H. et al., Dendritic cell subsets generated from CD34+ hematopoietic progenitors can be transfected with mRNA and induce antigen-specific cytotoxic T cell responses. J Immunol Methods. 2004 Feb. 15; 285(2):171-80; Awasthi S, Cox R A., 2003. Transfection of murine dendritic cell line (JAWS II) by a nonviral transfection reagent. Biotechniques. 35:600-2, 604; Ju D W. et al., 2001. Interleukin 18 transfection enhances antitumor immunity induced by dendritic cell-tumor cell conjugates. Cancer Res. 61:3735-40; and Chang C C. et al., 2000. Monocyte-derived CD1a+ and CD1a− dendritic cell subsets differ in their cytokine production profiles, susceptibilities to transfection, and capacities to direct Th cell differentiation. J. Immunol. 165: 3584-91).

The method of the present invention may be practiced by damaging according to the teachings of the present invention any of various quantities of the antigen-bearing cells so as to generate immunogenic cells of the present invention.

Damaging the antigen-bearing cells may be effected by applying the cell-damaging treatment to a quantity of the antigen-bearing cells, or to a tissue which includes and/or is formed by the antigen-bearing cells, having a volume selected from a range of about 0.0014 to about 34 cubic centimeters, more preferably having a volume selected from a range of about 0.014 to about 3.4 cubic centimeters, more preferably having a volume selected from a range of about 0.014 to about 0.34 cubic centimeters, and most preferably having a volume selected from a range of about 0.014 to about 0.034 cubic centimeters. It will be appreciated that since the density of cells/tissues is about that of water, i.e. about 1 gram per cubic centimeter, the latter volume range corresponds, for example, to a weight range of about 0.014 to about 0.034 grams.

As used herein the term "about" refers to ±10%.

As is described and illustrated in Example 2 of the Examples section which follows, lethal, metastatic cancer was successfully treated in mice according to the presently taught method by freeze-thawing a mass of tissue formed by antigen-bearing cells, i.e. a tumor, having a diameter of 3 to 4 millimeters. Assuming a spherical shape, a tumor 3 to 4 millimeters in diameter has a volume of about 0.014 to 0.034 cubic centimeters, and, assuming a density of 1 gram per cubic centimeter, has a mass of about 14 to about 34 milligrams.

Preferably, the method is performed by damaging according to the teachings of the present invention antigen-bearing cells, or of a tissue which includes and/or is formed by the antigen-bearing cells, having a weight whose ratio to the weight of the subject is selected from a range of about 0.000056:1 to about 0.0136:1, more preferably from a range of about 0.00007 to about 0.0109, more preferably from a range of about 0.00014 to about 0.00544, more preferably from a range of about 0.00028 to about 0.00272, and most preferably from a range of about 0.00056 to about 0.00136.

As is described and illustrated in Example 2 of the Examples section which follows, lethal, metastatic cancer was successfully treated in mice (average weight of about 25 grams), according to the presently taught method by freeze-thawing about 14 to about 34 milligrams of tumor tissue, which corresponds to damaging according to the teachings of the present invention a tissue formed by antigen-bearing cells having a weight whose ratio to that of the subject is selected from a range of about 0.00056 to about 0.00136.

The method of the present invention may be effectively practiced by administering to the subject APCs of the present invention at any of various total doses, and/or daily doses administered at any of various inter-dose intervals. Preferably, each dose of APCs administered to the subject is administered following, preferably as soon as possible, following application of a cell-damaging treatment to antigen-bearing cells of the present invention.

Preferably, the total number of APCs of the present invention which are administered to the subject is selected from a range of about $2 \times 10^5$ to about $6 \times 10^7$ cells, more preferably from a range of about $2.5 \times 10^5$ to about $4.8 \times 10^7$ cells, more preferably from a range of about $5 \times 10^5$ to about $2.4 \times 10^7$ cells, more preferably from a range of about $1 \times 10^6$ to about $1.2 \times 10^7$ cells, and most preferably from a range of about $2 \times 10^6$ to about $6 \times 10^6$ cells.

Preferably, the APCs are administered to the subject as a daily dose selected from a range of about $1 \times 10^5$ to about $2 \times 10^7$ cells per day, more preferably from a range of about $1.25 \times 10^5$ to about $1.6 \times 10^7$ cells per day, more preferably from a range of about $2.5 \times 10^5$ to about $8 \times 10^6$ cells per day, more preferably from a range of about $5 \times 10^5$ to about $4 \times 10^6$ cells per day, and most preferably from a range of about $1 \times 10^6$ to about $2 \times 10^6$ cells per day.

As is described and illustrated of Example 2 of the Examples section below (e.g. refer to FIGS. 4, 1 and 2, respectively), the method of the present invention may be effectively practiced, for example, by administration of APCs of the present invention as a single daily dose of $2 \times 10^6$ cells, as two daily doses of $1 \times 10^6$ cells at an inter-dose interval of 7 days, or as three daily doses of $2 \times 10^6$ cells at inter-dose intervals of 7 days.

The APCs may be administered to the subject in any of various daily/total doses per weight of the antigen-bearing cells, and/or per weight of a tissue which includes, and/or is formed by, the antigen-bearing cells.

Preferably, the APCs are administered to the subject as a daily dose per weight of the antigen-bearing cells, and/or per weight of a tissue which includes or is formed by the antigen-bearing cells, which is selected from a range of about $2.94 \times 10^6$ to about $1.43 \times 10^9$ cells per gram per day, more preferably from a range of about $3.67 \times 10^6$ to about $1.14 \times 10^9$ cells per gram per day, more preferably from a range of about $7.35 \times 10^6$ to about $5.72 \times 10^8$ cells per gram per day, more preferably from a range of about $1.47 \times 10^7$ to about $2.86 \times 10^8$ cells per gram per day, and most preferably from a range of about $2.94 \times 10^7$ to about $1.43 \times 10^8$ cells per gram per day Preferably, the total dose of APCs administered to the subject per weight of the antigen-bearing cells, and/or per weight of a tissue which includes and/or is formed by the antigen-bearing cells, is selected from a range of about $5.88 \times 10^6$ to about $4.29 \times 10^9$ cells per gram, more preferably from a range of about $7.35 \times 10^6$ to about $3.44 \times 10^9$ cells per gram, more preferably from a range of about $1.47 \times 10^7$ to about $1.72 \times 10^9$ cells per gram, more preferably from a range of about $2.94 \times 10^7$ to about $8.58 \times 10^8$ cells per gram, and most preferably from a range of about $5.88 \times 10^7$ to about $4.29 \times 10^8$ cells per gram.

As is described and illustrated in Example 2 of the Examples section which follows, lethal, metastatic cancer was successfully treated in mice by freeze-thawing antigen-bearing cells of the present invention, i.e. a tumor tissue, having a mass of about 14 to about 34 milligrams, by administration of APCs of the present invention in daily doses of 1 million to 2 million cells per day, and as a total dose of 2 million to 6 million cells. This corresponds to a daily dose of APCs per weight antigen-bearing cells of about 29.4 million to about 143 million cells per gram, and to a total dose of APCs per weight antigen-bearing cells of about 58.8 million to about 429 million cells per gram.

It will be appreciated that the method of the present invention can be applied to treat a disease of the present invention, such as a metastatic/potentially metastatic malignancy, in a subject the size of a human according to the above-described teachings. A dose of one to two million APCs in a mouse (about 25 grams body weight) corresponds to a dose per body weight of 40 to 80 million cells per kilogram, whereas such a dose in a 70 kg human corresponds to an approximately 2.800-fold lower dose per body weight. Nevertheless, as is well established in the art, T-lymphocytes, the cell type mediating target antigen-specific immunoreactivity against a target cell population according to the presently taught method, have the intrinsic function of rapidly and extensively proliferating according to immunophysiological need following antigen-specific activation thereof. For example, as is demonstrated in Example 2 of the Examples section which follows (refer, for example, to FIG. 4), in the context of the treatment method of the present invention, at least 65 percent of anti-tumor CTLs underwent at least 7-8 rounds of cell division within only the first four days following treatment via combined cryoablation and intratumoral dendritic cell injection. Furthermore, it was shown while reducing the present invention to practice that administration of APCs of the present invention via systemic routes (e.g. intravenous, intraperitoneal), markedly fails to achieve significant therapeutic effect. Hence, the presently disclosed reduction to practice teaches that the critical events responsible for triggering target antigen-specific immunoreactivity against a target cell population, such as cells of a lethal, metastatic malignancy, according to the presently taught method occur essentially exclusively within a cell aggregate of the present invention, such as a tumor tissue damaged according to the teachings of the present invention into which APCs of the present invention have been injected, and are therefore significantly independent of systemic parameters, such as total body weight. Hence, in light of the fact that the mechanisms triggering the target cell population reduction/growth-inhibition/elimination effects mediated by the method of the present invention occur locally in the area of a cell aggregate of the present invention, and not systemically, and in light of the potent capacity of activated T-lymphocytes to rapidly and extensively proliferate according to immunophysiological need following antigen-specific activation thereof, it will be appreciated that the method of the present invention may be effectively practiced where the subject is considerably larger than a mouse, such as human.

Thus, the method of the present invention may be used to effectively treat a metastatic/potentially metastatic tumor in a 70 kg human subject by freeze-thawing in the subject at least 0.014 grams of tumor tissue, and injecting into the freeze-thawed tumor tissue a total dose of about 58.8 million to about 429 million APCs per gram of freeze-thawed tumor tissue, in the form of single-day doses per weight freeze-thawed tumor tissue of about 29.4 million to about 143 million APCs per gram per day, and optionally repeating the freeze-thawing and APC administration once or twice at 7 day intervals between freeze-thawing/APC administration treatments.

It will be appreciated that the metastatic load per body weight in the 3LL-D122 mouse lung cancer model employed while reducing the present invention to practice is far greater than that generally found in a human patient, in particular a human lung cancer patient. It can be seen in FIG. 2 of the following Examples section that lung metastasis loads in the 3LL-D122 model reach a weight of 400 milligrams, which corresponds to 1.6 percent of a mouse's body weight (25 grams), and therefore to a 1.1 kilogram metastasis load in a 70 kilogram human, which is a particularly massive load in the context of a human cancer, such a human lung cancer. Thus, the capacity of the presently taught treatment method to very effectively prevent such aggressive metastatic spread in the mouse model highlights the great antigen-specific immunity induction capacity of the method, and clearly indicates that treating a subject bearing a cancer, such as a human bearing a metastatic/potentially metastatic cancer, according to the present method can be reasonably expected to achieve significant therapeutic effect, particularly in view of the fact that both human tumor freeze-thawing/cryoablation, and culturing and administration of human APCs, such as immature dendritic cells, are routinely practiced in the art.

As is described hereinabove, while reducing the present invention to practice it was uncovered that treatment of tumor-bearing mammals with combined tumor cryoablation and intratumoral dendritic cell administration specifically induces maximal levels of IFN-gamma producing Th1 cells relative to either treatment alone or combined tumor cryoablation and intravenous dendritic cell administration.

Thus, the disease treatment method of the present invention may advantageously comprise the step of inducing an increase in levels of Th1 cells in the subject to thereby enhance damaging or killing of the target cell population. Inducing the increase in the levels of the Th1 cells may be effected prior to, concomitantly with, or following administration of the antigen-presenting cells to the subject.

Th1 cells are known in the art as being a CD4+/helper T-cells which express one or more pro-inflammatory cytokine so as to promote cellular immunity (e.g. CTL-mediated immunity), as opposed, for example, to humoral (e.g. antibody-mediated) immunity.

Preferably, the pro-inflammatory cytokine is an interferon, more preferably interferon-gamma (IFN-gamma). Examples of pro-inflammatory cytokine include without limitation IL-2, IL-12, tumor necrosis factor-alpha (TNF-alpha), and IFN-alpha.

Any one of various methods known to the skilled artisan may be employed for increasing levels of Th1 cells in a mammalian subject, such as a human. For example, administration of a suitable cytokine in a suitable dose to a subject can be used to increase levels of Th1 cells in the subject. Examples of cytokines which can be administered to a subject so as to increase Th1 cell levels in the subject include, without limitation, IL-12, IL-18, interferon-gamma, TNF-alpha and peptide-25 (Takatsu K, Kariyone A., 2003. Int Immunopharmacol. 3:783-800). Ample guidance is provided in the literature of the art for selecting and administering a Th1-promoting cytokine to a subject so as to increase levels of Th1 cells in the subject (refer, for example, to: Constant S L, Bottomly K., 1997. Annu Rev Immunol. 15:297-322).

As described hereinabove, the method of the present invention can be used for treating in a subject any of various diseases such as a tumor, a precancer, a cancer, an intracellular pathogen infection, and an autoimmune disease, whose pathology involves a pathological cell population of the subject which specifically includes at least one antigen.

One of ordinary skill in the art, such as a physician or a veterinarian, will possess the necessary expertise for applying the teachings of the present invention, optionally, as suitable, in combination with standard medical treatments such as surgical, radiotherapeutic and/or chemotherapeutic treatments, for achieving effective treatment of a disease of the present invention in a subject of the present invention.

Preferably, the method is used to treat a tumor.

Examples of tumors amenable to treatment via the method of the present invention include benign tumors, malignant tumors and/or inflammatory tumors.

Preferably the tumor is a malignant tumor/cancer, and most preferably a metastatic/potentially metastatic tumor/cancer.

Preferably, the cancer is a carcinoma, a melanoma, a lung cancer, a skin cancer, a sarcoma, or a liver cancer.

Most preferably, the cancer is a lung carcinoma or a melanoma.

Figure 5:
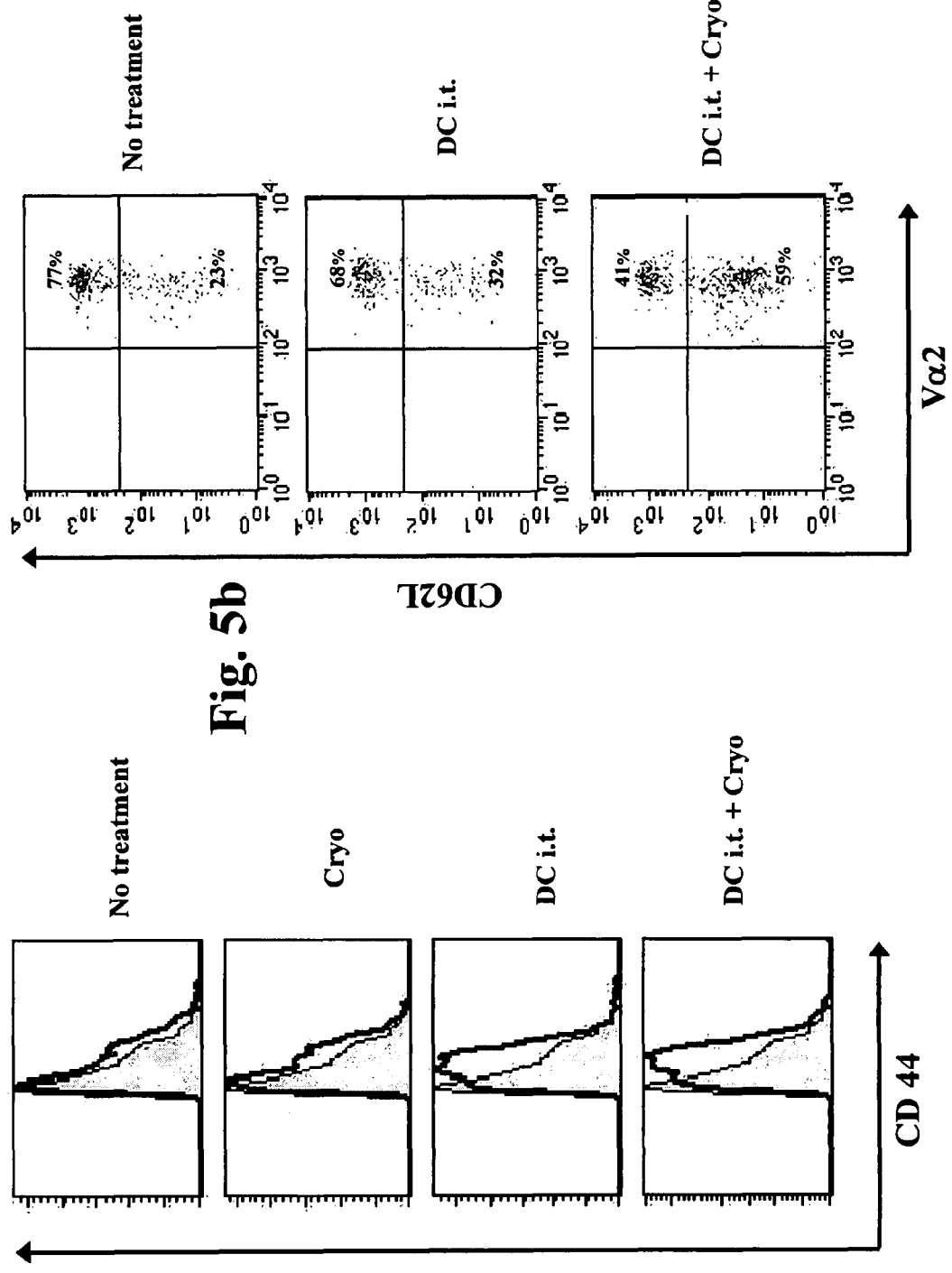
FIGS. 5a-b are a series of FACS histograms depicting that intratumoral injection of dendritic cells, alone or following cryoablation, increases the subset of $CD8^+CD44^+$ cells, as compared to cryoablation alone or no treatment (FIG. 5a), and that combined cryoablation and intratumoral dendritic cell injection decreases the subset of $CD8^+CD62L^+$ cells, as compared to cryoablation alone or no treatment (FIG. 5b). OT-I-derived naïve $CD8^+$ lymphocytes were transferred into B16-MO5 melanoma-bearing C57BL/6 mice that were treated, as indicated, via intratumoral cryoablation alone (Cryo), intratumoral dendritic cell injection (DC i.t.), or combined cryoablation and intratumoral dendritic cell injection (DC i.t.+Cryo). The control group received adoptively transferred cells only with no additional treatment. The adoptive transfer resulted in tumor rejection in 50 to 60 percent of mice. Sixty days following tumor rejection draining lymph node-derived lymphocytes were analyzed by flow cytometry, via gating on $CD8^+Valpha2^+$ cells, for surface expression of CD44 (FIG. 5a), or of Valpha2 and anti-CD62L (FIG. 5b). Results are shown for a representative mouse from groups of three, and similar results were obtained in three independent experiments.

As is described and illustrated in Example 2 of the Examples section which follows, the method of the present invention can be used to effectively treat in a mammalian subject a lethal, metastatic lung carcinoma (refer, for example, to FIGS. 2-3), and lethal, metastatic melanoma (refer, for example, to FIGS. 5a-b).

As is demonstrated in the literature of the art combined induction of tumor necrosis (via harmful prior art irradiation- or antineoplastic agent-based methods) and intratumoral dendritic cell administration may be used to treat sarcomas (Teitz-Tennenbaum S. et al., 2003. Cancer Res. 63:8466-75; Shin J Y. et al., 2003. Histol Histopathol. 18:435-47), and liver tumors (Chen Z. et al., J Gene Med. 2004 Dec. 6; [Epub ahead of print]).

Examples of cancers which can be treated using the method of the present invention include adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, meningioma; multiple endocrine neoplasia; myeloid malignancy, predisposition to; myxosarcoma, neuroblastoma; osteosarcoma; ovarian cancer; ovarian cancer, serous; ovarian carcinoma; ovarian sex cord tumors; pancreatic cancer; pancreatic endocrine tumors; paraganglioma, familial nonchromaffin; pilomatricoma;

pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, etc.

Precancers are well characterized and known in the art (refer, for example, to Berman J J. and Henson D E., 2003. Classifying the precancers: a metadata approach. BMC Med Inform Decis Mak. 3:8). Classes of precancers amenable to treatment via the method of the present invention include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

The method of the present invention is particularly suitable for treatment of precancers whose pathology involves large lesions, for example polyps, such as those described hereinabove, which can be conveniently localized and subjected to a cell-damaging treatment of the present invention.

It will be appreciated that the presently disclosed method is clearly inventive and non-obvious since the prior art clearly teaches away from the method of the present invention. For example, the prior art clearly and emphatically teaches that exposing APCs, such as dendritic cells, to antigen-bearing cells damaged according to the teachings of the present invention (as opposed to exposing them to cell lysates), as is distinctly taught by the present invention completely fails to confer upon such APCs the capacity to induce proliferation of T-lymphocytes (Rad et al., 2003. Cancer Res. 63:5143-5150), and the capacity to induce pro-inflammatory cytokine secretion by T-lymphocytes (Strome S E. et al., Cancer Res. 62:1884-9), both of which being critical for induction of immunity via such APCs against such antigen-bearing cells. As such, in view of the prior art, one ordinarily versed in the art would clearly not be motivated to practice the present invention.

It will be further appreciated that the presently disclosed method is clearly inventive and non-obvious due to the presently disclosed unpredictable discovery made while reducing the present invention to practice that the method of the present invention is unpredictably and surprisingly effective. Namely, as is described in Example 2 of the Examples section below, damaging a pathological cell population of the present invention according to the teachings of the present invention, i.e. freeze-thawing of a primary tumor of a lethal metastatic cancer in a subject of the present invention, in combination with administration of APCs of the present invention to the subject according to teachings of the present invention, i.e. intratumoral administration of immature autologous dendritic cells, relative to either treatment alone uniquely results in stable long-term survival of any of the treated subjects, such survival being significantly achieved in a large proportion (50 percent) of the treated subjects (refer, for example, to FIG. 3), and results in synergistic generation of anti-tumor CTLs (refer, for example to FIG. 1).

Thus, the present invention provides a novel and non-obvious method of using combined vaccination with APCs, such as dendritic cells, and localized cell ablation, such as cryoablation, for effectively treating in a mammalian subject, such as a human subject, a disease, such as a cancer, a pre-cancer, a tumor, an intracellular pathogen infection, or an autoimmune disease, whose pathology involves a pathological cell population which is characterized by at least one antigen.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W.H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

General Materials and Methods

Experimental strategy overview: The immunostimulatory, antimetastatic, and pro-survival effects of treatment of tumor-bearing mice via cryoablation only, dendritic cell administration only, or combined cryoablation and dendritic cell administration were investigated using as a murine tumor model a lethal, spontaneously metastatic lung carcinoma line. The immune mechanisms elicited by the experimental treatments were investigated using as a murine tumor immunity model a transfectant melanoma cell line expressing an exogenous antigen, and adoptive transfer of CD8$^+$ T-lymphocytes specific for the exogenous antigen.

Mice: Eight- to twelve-week old C57BL/6 mice and OT-1 TCR (Valpha2/Vbeta5) transgenic mice, encoding a TCR specific for the H-2K$^b$-restricted ovalbumin$_{257-265}$ peptide SIINFEKL (SEQ ID NO: 1; Hogquist K A. et al., 1994. Cell 76:17-27) were bred in the Weizmann Institute. All mouse experiments were approved and conducted under Institutional Animal Care and Use Committee guidelines.

Cell lines: 3LL-D122 Lewis lung carcinoma-based clones and B16 melanoma-based clones, both of C57BL/6 origin, were maintained in DMEM supplemented with 10 percent FCS, L-glutamine, sodium pyruvate, non-essential amino acids and penicillin/streptomycin. Clone 3LL-D122 is a low H2-K$^b$-expressor which is highly metastatic and poorly immunogenic. Clone K$^b$39.5 is an immunogenic H2-K$^b$- transfectant line derived from parental 3LL-D122. B16-MO5 is an ovalbumin-expressing transfectant melanoma line derived from the parental melanoma line B16-F1. Cell lines K$^b$39.5 and B16-MO5 were maintained in culturing medium including 500 micrograms per milliliter G-418.

Metastatic/lung cancer model (3LL-D122): As a tumor model for investigating the therapeutic efficacy of the experimental treatments, 8-11 C57BL/6 mice per group, were inoculated intra-footpad (i.f.p.) with two-hundred thousand 3LL-D122 cells per mouse. When the resultant tumor reached about 8 millimeters in diameter, which corresponds to a stage at which untreated mice have spontaneously developed pulmonary metastases, the tumor-bearing leg was amputated below the knee (Eisenbach L. et al., 1984. Int J Cancer 34:567-73). Mice were monitored daily and sacrificed when moribund or 23-30 days postamputation, in accordance with the death of the control group. Lung metastatic load was assessed by weighing. Survival was defined as the day when mice were sacrificed.

Melanoma model (B16-MO5): As a model for investigating immune mechanisms elicited by the experimental treatments, one million B16-MO5 cells per mouse were inoculated intra-footpad in C57BL/6 mice. Ten days later, the mice were treated via cryoablation only, intratumoral dendritic cell injection, or combined cryoablation and intratumoral dendritic cell injection, and were injected with CD8$^+$ T-lymphocytes from OT-1 transgenic mice. Mice having rejected the B16-MO5 tumor (about 50 percent of total) were re-challenged at day 60 post-rejection, by inoculation with one million B16-F1 cells injected subcutaneously in the upper back. Tumor take and growth were then monitored over 90 days.

Generation of dendritic cells from mouse bone marrow: A previously described procedure (Lutz M B. et al., 1999. J Immunol Methods 223:77-92) was used with minor modifications. Four million C57BL/6 bone marrow cells were cultured in 100 millimeter bacteriological plates (Falcon) in 10 milliliters DC medium supplemented with 200 units per milliliter recombinant murine granulocyte-macrophage colony-stimulating factor (r-m GM-CSF; Prospect, Israel). On day 3, another 10 milliliters of DC medium containing 200 units per milliliter GM-CSF were added to the plates. On day 6, half of the culture supernatant was replaced with fresh DC medium containing 200 units per milliliter GM-CSF. On day 8, non-adherent cells were collected, resuspended in 10 milliliters fresh DC medium containing 100 units per milliliter GM-CSF and seeded in 100 millimeter tissue culture plates (Falcon). On day 9, non-adherent cells with the typical characteristics of immature dendritic cells (>95 percent CD11c$^+$, CD80$^{low}$, CD86$^{low}$, MHC II$^{low}$) were harvested, washed, and resuspended in PBS at 40 million cells per milliliter prior to injection.

Treatment modes: When tumors reached 3-4 millimeters in diameter (2 weeks post-inoculation for 3LL-D122-type tumors), the mice were treated via cryoablation alone or in combination with subsequent intratumoral (i.t.), intraperitoneal (i.p.), or intravenous (i.v.) dendritic cell injection. For treatment via dendritic cell injection for cytotoxicity assays in the 3LL-D122 model, the animals were injected with one million immature dendritic cells. For metastasis development and survival assays, two million immature dendritic cells were injected in a volume of 50 microliters. Negative control groups for dendritic cell injection received PBS injections instead. Anaesthetized mice (Ketamine-HCL, 100 mg/kg, i.p.) underwent cryoablation by application of mild pressure to the tumor for 10 seconds with frozen tweezers pre-chilled in liquid nitrogen, until formation of an ice ball about 5 millimeters in diameter. To ensure complete thawing of the frozen tumor prior to vaccination, the dendritic cells were administered 60 minutes after administration of cryoablation.

For analyzing the effects of experimental treatments on anti-tumor cytotoxic capacity of CTLs of treated 3LL-D122 tumor-bearing mice, the mice were treated twice with a one-week interval between treatments.

For analyzing the effects of experimental treatments on metastatic load, 3LL-D122 metastatic tumor-bearing mice were treated 3 times at weekly intervals.

In the B16-MO5 model, mice were treated once followed by adoptive transfer of OT-1 CD8$^+$ T-lymphocytes.

In-vitro cytotoxicity assay: For cytotoxic T lymphocyte (CTL) assays, spleens were harvested from mice ten days after the second experimental treatment, and splenocyte suspensions were restimulated for 5 days on mitomycin C (80 micrograms per milliliter)-treated and irradiated (5000 rads) K$^b$39.5 tumor monolayers. Viable effector cells were centrifugally isolated over a Lympholyte-M cushion (Cedarlane, Canada), resuspended in RPMI supplemented with 10 percent FCS, glutamine, sodium pyruvate, nonessential amino acids, and 2-mercaptoethanol, and were mixed with 5,000 [35S]-L-methionine labeled target cells for 5 hours as previously described (Carmon L. et al., 2002. J Clin Invest. 110: 453-62). Percentage of specific lysis was calculated as follows: percent lysis=(cpm in experimental well–cpm spontaneous release)/(cpm maximal release–cpm spontaneous release)×100.

Adoptive transfer of OT-1 CD8+ T-lymphocytes and flow cytometry: CD8+ T-lymphocytes from OT-1 mouse spleens were purified (>95 percent) via magnetic cell sorting using MACS (Miltenyi, Germany), according to the manufacturer's instructions. Two million CD8+ T-lymphocytes were injected intravenously into tumor-bearing C57BL/6 recipients, previously treated as described above. In some experiments, cells were labeled with carboxyfluorescein diacetate succinimidyl ester (CFSE; Molecular Probes, OR) according to the manufacturer's instructions. Animals were sacrificed on the indicated days following cell transfer or on day 60 following tumor rejection. Cells from draining lymph nodes (LNs) and spleens were stained with anti-CD8-APC, phycoerythrin (PE)-conjugated anti-Valpha2 mAb, fluorescein isothiocyanate (FITC)-conjugated anti-CD44 mAb, PE-conjugated anti-CD62L mAb, FITC-conjugated anti-CD69 or isotype control mAb (BD PharMingen, CA), and were analyzed using a FACSort fluorescence-activated cell sorter (FACS) and CellQuest software (BD Biosciences). CFSE fluorescence levels were detected on CD8+ Valpha2+-gated populations.

Statistical analysis: The data obtained in the CTL assays were analyzed by one-way ANOVA and significance was assessed by the Tukey-Kramer test. Statistical analysis of the metastatic loads was performed using an unpaired Welch t-test. Dunnett multiple comparison test and log-rank test were applied for survival analysis.

Example 2

Synergistic and Highly Effective Treatment of Lethal, Metastatic Cancer Via Combined Tumor Cryoablation and Intratumoral Dendritic Cell Administration Background: No optimal therapy exists for treatment of numerous types of cancers, in particular for treatment of metastatic cancers. While localized cell ablation, in particular cryoablation, of prostate, uterine, renal and hepatic primary tumors and metastases is considered a minimally invasive treatment demonstrating a low complication rate in comparison to conventional surgery for treatment of localized accessible lesions, this type of therapy has no systemic effect, and hence cannot be used to treat inaccessible, disseminated, or poorly localized lesions, nor to prevent local disease recurrence. Immunotherapeutic approaches, on the other hand, such as those involving antigen-presenting cell (APC) vaccination, while being less suited for treatment of bulky lesions, such as primary tumors, than localized cell ablation methods, are potentially useful for inducing systemic anti-cancer immunity. As such immunotherapies involving APC vaccination are potentially suitable for treatment of inaccessible, disseminated, microscopic, recurrent and/or poorly localized lesions, such as metastatic lesions. Thus, a potentially optimal strategy for treating cancer would be to combine localized tumor ablation, such as tumor cryoablation, with APC vaccination so as to achieve treatment of accessible, localized lesions, prevention of locally recurrent disease, and treatment of inaccessible, disseminated and/or poorly localized lesions. This strategy presents the advantages of circumventing, or minimizing, the use of the standard locally and systemically toxic therapies, such as chemotherapy or radiotherapy, and of being practicable using minimally invasive, simple techniques, such as catheter-based cell ablation methods, such as catheter cryoablation, combined with APC vaccination. While various approaches for using combined localized cell ablation and APC vaccination have been proposed or attempted in the prior art, these have been suboptimal for various reasons, as described above. While reducing the present invention to practice, a method of using localized cell ablation, in particular tumor cryoablation, combined with APC vaccination to synergistically treat cancer relative to either treatment alone was unexpectedly uncovered, thereby overcoming the limitations of the prior art, as described below.

Experimental Results:

Treatment of a mammal bearing a lethal metastatic tumor via combined cryoablation and intratumoral dendritic cell injection, compared to either treatment alone, induces maximal/synergistic generation of specific antitumor cytotoxic CTLs in the mammal: The capacity of combined cryoablation and dendritic cell immunotherapy to induce specific anti-tumor CTL responses in 3LL-D122 tumor-bearing mice was examined by inducing tumors in mice, subjecting the mice to experimental treatment, harvesting splenocytes of treated mice, restimulating the harvested splenocytes with H2-$K^b$-transfected 3LL-D122 cells, and challenging the restimulated splenocytes with 3LL-D122 target cells in a cytotoxicity assay. The results, shown in FIG. 1a, showed induction of anti-tumor CTL responses following treatment via intratumoral injection of dendritic cells alone at effector-to-target ratios (E:T) of 100:1 and 50:1 (p=0.001), compared to no treatment or treatment via cryoablation alone or combination with intravenous dendritic cell administration, both of which failed to induce any anti-tumor CTL responses. Very unexpectedly, however, maximal and high-level specific anti-tumor CTL activity was induced when dendritic cells were injected intratumorally following in-situ cryoablation, even though cryoablation alone resulted in slightly decreased anti-tumor CTL responses compared to the no-treatment control. Induction of anti-tumor CTL generation achieved using combined cryoablation and intratumoral dendritic cell injection was synergistic at a target-to-effector ratio of 25:1, relative to either treatment alone. Compared to treatment via intratumoral dendritic cell injection alone, the combined cryoablation-APC vaccination treatment induced significantly higher anti-tumor cytolytic capacity at all E:T ratios (p=0.005). Controls showed that anti-tumor CTLs were tumor-specific, and had the capacity to lyse 3LL-D122 cells, but not irrelevant B16 melanoma cells (FIG. 1b).

Treatment of a metastatic and lethal primary tumor via combined cryoablation and intratumoral dendritic cell injection completely inhibits metastatic spread, and results in a fifty percent prolonged survival rate, whereas neither treatment alone, nor treatment via intraperitoneal dendritic cell injection alone or in combination with cryoablation led to prolonged survival, or to complete prevention of metastatic spread: To examine the effect of various experimental treatments on development of spontaneous lung metastases, mice were inoculated intra-footpad with 3LL-D122 cells, and, upon reaching a size of 3-4 millimeters in diameter, the resultant primary tumors were treated either by cryoablation only, intratumoral or intraperitoneal dendritic cell injection only, or by cryoablation in combination with either intratumoral or intraperitoneal dendritic cell injection. When tumors reached a diameter of 8 mm, tumor-bearing feet were amputated, and, 23-30 days later, in accordance with the death of the control group, the mice were sacrificed and metastatic loads were determined by lung weighing. The results of these experiments, summarized in FIG. 2, showed that treatment via intratumoral dendritic cell injection alone was found to moderately reduce metastatic spread, as compared to no treatment control (p=0.0019), cryoablation (p=0.0034) alone or in combination with intraperitoneal dendritic cell injection, or intraperitoneal dendritic cell injection alone. However, in accordance with the cytotoxicity assay results, combined cryoablation and intratumoral dendritic cell injection of the primary tumors was surprisingly found to completely prevent metastasis development, as compared to treatment via intratumoral dendritic cell injection alone (p<0.0001).

Alternatively, the survival of the mice following surgical removal of primary tumor-bearing feet was monitored. As shown in FIG. 3, about 50 percent of mice that were treated by combined cryoablation and intratumoral dendritic cell injection displayed stable and prolonged survival (p=0.005). Namely, five out of ten mice from the group that underwent combined cryoablation and intratumoral dendritic cell injection were alive at day 32 following primary tumor removal, whereas none of the mice subjected to any of the other experimental treatments survived at that time point.

Thus, treatment of metastatic and lethal primary tumors via combined cryoablation and intratumoral dendritic cell injection, unlike either treatment alone or any other experimental treatment described herein, unexpectedly resulted in generation of CTLs in treated mice having maximal/synergistic specific anti-tumor cytotoxicity, and uniquely resulted in prolonged survival and complete prevention of metastatic spread of treated mice, such prolonged survival being observed in a large proportion (50 percent) of the treated mice.

Figure 4:
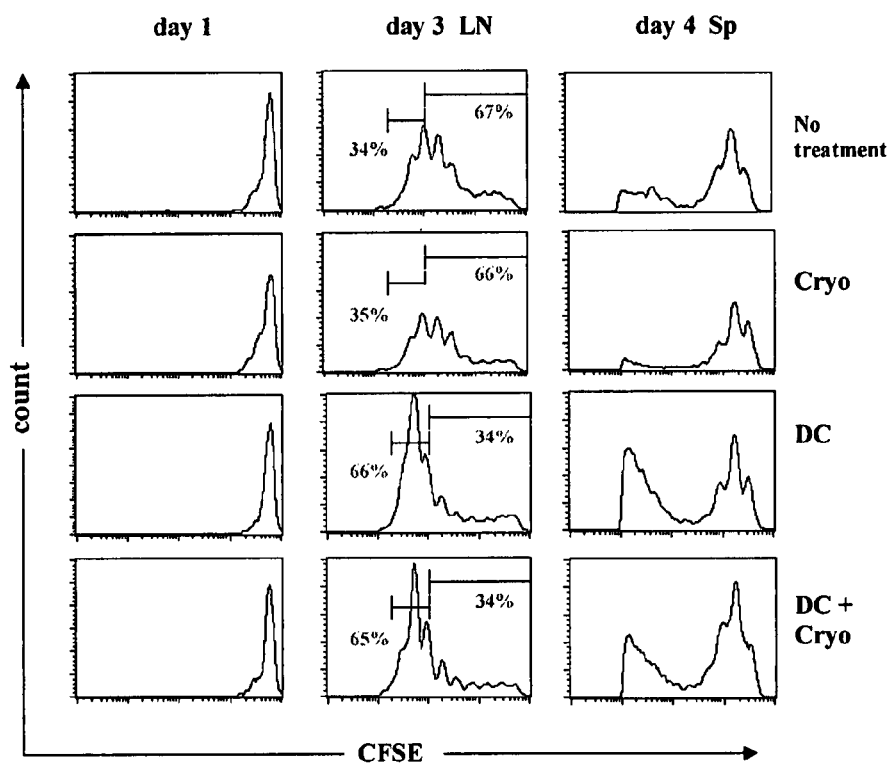
FIG. 4 is a series of FACS histograms depicting that treatment of B16-MO5 tumor-bearing mice via intratumoral dendritic cell injection alone (DC) or cryoablation (DC+Cryo), but not via cryoablation alone (Cryo), induces vigorous proliferation of adoptively transferred CFSE-labeled OT-1 $CD8^+$ T-lymphocytes in the mice. The extent of cell division, based on CFSE fluorescence, in the OT-I-derived naïve $CD8^+$ lymphocytes was examined 1 day (day 1), 3 days (in lymph node; day 3 LN) and 4 days (in spleen; day 4 Sp) following adoptive transfer into C57BL/6 tumor-bearing mice treated via cryoablation alone (Cryo), intratumoral dendritic cell injection (DC), or combined cryoablation and intratumoral dendritic cell injection (DC+Cryo). Histograms displaying CFSE fluorescence are gated on $CD8^+$ lymphocytes. Results are shown for a representative mouse from groups of three, and similar results were obtained in three independent experiments.

Treatment of tumor-bearing mammals via intratumoral dendritic cell injection alone or following cryoablation results in induction of memory ($CD44^{high}$, $CD62L^{low}$) anti-tumor CTLs: The mechanism of anti-tumor immunity induced by the experimental treatment was then analyzed using an adoptive transfer model. Naïve $CD8^+$ T-lymphocytes bearing the OT-1 TCR specific for the $H2-K^b$-restricted peptide ovalbumin$_{257-265}$ (SIINFEKL; SEQ ID NO: 1), obtained from OT-I transgenic mice, were transferred into C57BL/6 mice inoculated with the ovalbumin-expressing melanoma tumor line B16-MO5. The treatment effect on the proliferation kinetics of the adoptively transferred cells was assessed by pre-labeling the adoptively transferred cells with the fluorophore CFSE. Upon cell division, CFSE is distributed equally between daughter cells, allowing the resolution of up to eight cycles of cell division by flow cytometry. As shown in FIG. 4, treatment via cryoablation alone does not affect the proliferation profile of the adoptively transferred CTLs. In contrast, intratumoral dendritic cell injection, either alone or following cryoablation, triggered vigorous proliferation of adoptively transferred $CD8^+$ T-lymphocytes in draining lymph nodes (day 3) and spleens (day 4) of tumor-bearing mice, resulting in a proportion of cells that divided 7-8 times of 65-66 percent, as compared to only 34-35 percent in nontreated or cryotreated mice. To examine whether the extensive proliferation of these cells is accompanied by changes in their activation status, expression patterns of activation-related cell-surface molecules were evaluated. following primary tumor removal Expression of the early activation marker CD69, as well as of the adhesion molecules CD44 and CD62L were found to be comparable in all groups tested (data not shown). These findings therefore indicate that combined cryoablation and intratumoral dendritic cell injection does not increase the percentage of activated $CD8^+$ lymphocytes, but rather affects their proliferation to the same extent as intratumoral dendritic cell injection alone.

The fate of adoptively transferred $CD8^+$ T-lymphocytes was addressed in mice that were treated either via intratumoral dendritic cell injection alone or in combination with cryoablation. To this end, the phenotypes of memory $CD8^+$ T-lymphocytes were studied in mice on day 60 following adoptive transfer-induced tumor rejections. At this time point, memory $CD8^+$ T-lymphocytes express high levels of CD44 (Dutton R W. et al., 1998. Annu Rev Immunol. 16:201-23) whereas CD62L expression may vary from low/intermediate for the effector memory subset (Tme), to high for the central memory population (Tmc; Sallusto F. et al., 1999. Nature 401:708-12). Intratumoral injection of dendritic cells, alone or following cryoablation, increased the subset of $CD44^+$ $CD8^+$, as compared to cryoablation alone or no treatment (FIG. 5a). The percentage of $CD8^+CD44^+$ T-lymphocytes derived from naïve mice was comparable to that of cryotreated or untreated tumor-bearing mice (data not shown). Sixty days following tumor rejections, most (77 percent) adoptively transferred $CD8^+$ T-lymphocytes in untreated or cryotreated mice expressed high levels of CD62L, reflecting a naïve $CD44^{low}$, $CD62L^{high}$ cell population (FIGS. 5a-b, respectively). In contrast, $CD8^+$ T-lymphocytes derived from the mice following combined cryoablation and intratumoral dendritic cell injection were mainly (59 percent) CD62L-negative, supporting the existence of an effector memory $CD44^{high}$, $CD62L^{low}$ cell population (FIGS. 5a-b, respectively).

Combined cryoablation and intratumoral dendritic cell injection of OT-1 tumors confers optimal, high-level protection against parental tumor re-challenge in cured mice compared to either treatment alone: To examine the functional value of the anti-tumor memory, the mice that had survived primary B16-MO5 tumors following adoptive transfer and indicated treatments were re-challenged with secondary B16-F1 (ovalbumin negative) tumors and monitored for survival. As shown in Table 2, combined cryoablation and intratumoral dendritic cell injection protected 6/7 mice from the secondary tumors for more than 90 days (P=0.010 and P=0.029, compared with nontreated and cryotreated mice, respectively), whereas intratumoral dendritic cell injection alone was much less potent (3/8, P>0.5, compared with either nontreated or cryotreated mice) and cryoablation alone was essentially ineffective (1/7), similarly to no treatment (1/8). Hence, combined cryoablation and intratumoral dendritic cell injection induced an effector memory $CD8^+$ T-cell subset, which was probably important for protection against the secondary tumors.

Discussion: Cryosurgery has reemerged as an in-situ treatment for various, primarily urologic, malignancies (Han K R, Belldegrun A S., 2004. BJU Int. 93:14-8). This type of treatment, while useful for destruction of localized tumor masses, has negligible antimetastatic effect, [Hoffmann N E, Bischof J C., 2002. Urology 60 (2 Suppl 1):40-9], and in fact, numerous studies have suggested that cryosurgery is associated with decreased immunity, and with elevated metastasis (Hoffmann N E, Bischof J C., 2002. Urology 60 (2 Suppl 1):40-9; Urano M. et al., 2003. Cryobiology 46:238-45). There is evidence that by combining immunoadjuvants with cryosurgery one may augment the host systemic anti-tumor immune response. A short list of studies addressing this issue have involved intralesional injections of BCG in animal models and in clinical settings (Javadpour N. et al., 1979. J Natl Cancer Inst. 62:1479-81; Iavorskii V V. et al., 1988. Vopr Onkol. 34:799-803), and systemic administration of protein-bound polysaccharide in a murine model (Urano M. et al., 2003. Cryobiology 46:238-45).

TABLE 2

Combined cryoablation and intratumoral dendritic cell injection of OT-1 tumors confers optimal protection against parental tumor re-challenge in cured mice compared to either treatment alone

| Treatment | Number of rechallenged mice | Number of surviving mice (>90 days) | Percent surviving mice (>90 days) |
|---|---|---|---|
| no treatment | 8 | 1 | 12.5 |
| cryoablation | 7 | 1 | 14 |
| intratumoral dendritic cell injection | 8 | 3 | 37.5 |
| cryoablation+ intratumoral dendritic cell injection | 7 | 6 | 86 |

C57Bl/6 mice (15-16 per group) were inoculated intra-footpad with one million B16-MO5 transfectant cells per mouse. Ten days later, when the tumor reached 3-4 mm in diameter, the mice were treated as indicated and injected with OT-1 CD8+ T cells, as described under Materials and Methods. Mice that rejected the tumor were re-challenged, at day 60 post rejection, with one million parental B16-F1 cells subcutaneously in the upper back. Mouse survival was monitored for more than 90 days following re-challenge. P = 0.010 for [cryoablation + intratumoral dendritic cell injection]/[no treatment]; P = 0.029 for [cryoablation + intratumoral dendritic cell injection]/[cryoablation only]; P = 0.569 for [intratumoral dendritic cell injection only]/[no treatment] or [intratumoral dendritic cell injection only]/[cryoablation only], according to Fisher exact test.

The presently disclosed experiments are the first to address the influence of in-situ administration of immature dendritic cells following cryoablation of primary tumors on systemic anti-tumor immunity. The results surprisingly show that in-situ injection of immature non-loaded dendritic cells following cryosurgery, as opposed to cryoablation alone or the use of ex-vivo matured, antigen-loaded dendritic cells results in optimal generation of activated tumor-specific CTLs, antimetastatic effects, and prolongation of survival of treated mice (FIGS. 1-3).

Figure 6:
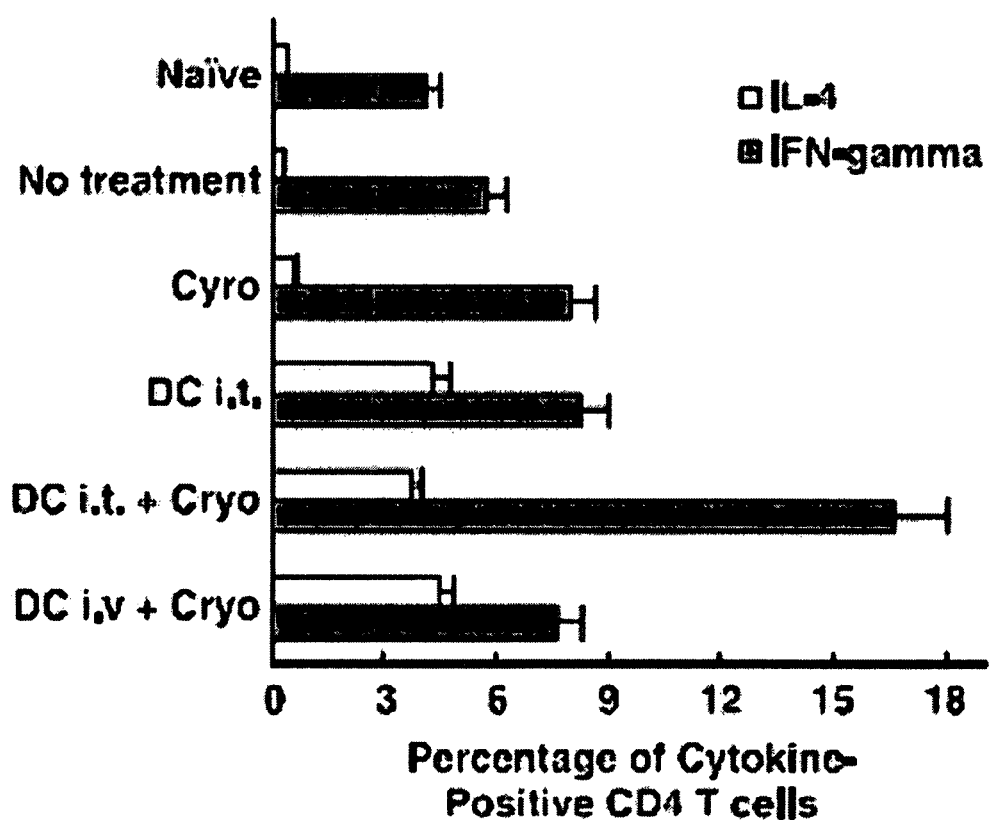
FIG. 6 is a histogram depicting intracellular IFN-gamma or IL-4 expression by CD4+ T-cells following stimulation with PMA and ionomycin. Eight days post-treatment, splenocytes were stimulated with PMA and ionomycin in the presence of brefeldin A. The cells were gated on CD4+ T-cells that expressed a given cytokine. Columns, means; bars plus/minus SD (n=3 per group).

A major advantage of combining cryoablation with intratumoral dendritic cell injection as described herein, is that the destruction of a large primary tumor mass at pre-metastatic/early metastatic stages by cryoablation leaves only a minimal metastatic/residual primary tumor burden which is tractable via cellular immunotherapy which by itself is inadequate to optimally treat the full tumor burden at time of treatment. Thus, ablation of the primary tumor may markedly enhance the chances of successful destruction of residual cells or distant metastases. Another major advantage of combining cryoablation with direct intratumoral dendritic cell injection is that it concomitantly results in exposure of the dendritic cells to physiological conditions which are particularly efficient for inducing their maturation into cells capable of inducing anti-tumor immunity, as well as in particularly efficient targeting of the dendritic cells to the target tumor cells. This is accomplished, respectively, by virtue of using cryotreatment to generate a large concentrated mass of necrotic tumor cells, such necrotic cells being particularly efficient at inducing maturation of dendritic cells capable of functionally presenting tumor antigens to lymphocytes; and as a result of injecting the dendritic cells directly into such a mass of necrotic tumor cells. Such efficient targeting is of importance since most studies present data showing that only a small proportion of dendritic cells injected by other routes arrived at the target organ (Barratt-Boyes S M. et al., 2000. J. Immunol. 164: 2487-95). With respect to the advantages of intratumoral dendritic cell injection, studies have shown that direct intratumoral injection of genetically modified dendritic cells, or co-administration of dendritic cells and adenoviral vector expressing CD40 ligand reduces the incidence and growth of tumors in pre-clinical models (Melero I. et al., 1999. Gene Ther. 6:1779-84; Kikuchi T. et al., 2000. Cancer Res. 60:6391-5). In agreement with these data, intratumoral administration of dendritic cells as described herein raised tumor-specific CTL and Th1 type CD4+ cells, and decreased metastatic burden in a spontaneous metastasis model while dendritic cells injected intravenously or intraperitoneally failed to do so (FIGS. 1, 2 and 6). The microenvironment of the freeze-thawed tumor contains inflammatory cytokines and is an excellent milieu for the maturation of dendritic cells into cells which will process and present a wide spectrum of tumor cell antigens in the context of type 1 cellular responses. Indeed, combined cryoimmunotherapy induced the highest levels of IFN-gamma-producing CD4+ cells (FIG. 6) as well as CTLs. The capacity of dendritic cells to expand cancer-directed immune responses is well documented while the mode of dendritic cell maturation and loading methods often determine the fate of the immune response toward either stimulation or tolerance (Schuler G. et al., 2003. Curr Opin Immunol. 15:138-47; Figdor C G. et al., 2004. Nat. Med. 10:475-80). Immature rather than mature dendritic cells are particularly efficient at antigen ingestion and processing (Figdor C G. et al., 2004. Nat. Med. 10:475-80). There is evidence that dying cells are captured fivefold better by immature compared to mature dendritic cells (Sauter B. et al., 2000. J Exp Med. 191:423-34). Fully mature dendritic cells, which express high levels of MHC and co-stimulatory molecules as well as produce large amounts of proinflamatory cytokines and IL-2 are optimal for induction of T-cell immunity (Lutz M B, Schuler G., 2002. Trends Immunol. 23:445-9). Furthermore, the mode of tumor cell death may determine whether T-lymphocyte activation or T-lymphocyte tolerance occurs. Current evidence suggests that necrotic rather than apoptotic cell death provides the necessary signals for the full activation of dendritic cells, which promotes T-cell responses (Sauter B. et al., 2000. J Exp Med. 191:423-34). Indeed, the presently disclosed findings indicate that compared to dendritic cell administration alone, cryoablation-induced necrotic tumor cell death prior to dendritic cell administration markedly enhances systemic anti-tumor immunity.

CD8+ T-lymphocytes play an essential role in anticancer immunity, and are the most specific and functionally active effector cells. A predominant role of CD8+ T-lymphocytes in tumor growth inhibition upon intratumoral administration of dendritic cells has been reported (Candido K A. et al., 2001. Cancer Res. 61:228-36). Utilizing adoptive transfer of purified CD8+ T-lymphocytes specific to a complex of H2-K$^b$ and the ovalbumin-derived peptide SIINFEKL (SEQ ID NO: 1) into melanoma-bearing mice, the kinetics of CD8+ T-lymphocyte proliferation following priming were presently elucidated. Intratumoral administration of the dendritic cells triggered robust proliferation of the transferred T-lymphocytes, as compared to cryoablation alone (FIG. 4). The extremely high affinity ($K_d=10^{-14}$) of the transgenic TCR to its complex could account for the lack of additional enhancement of the proliferation rate in mice that underwent combined cryoablation and intratumoral dendritic cell administration. T-lymphocyte clones with low-affinity TCRs are expanded by prolonged exposure to high doses of antigens (Anderton S M. et al., 2001. J Exp Med. 193:1-11). Therefore, one may assume that such polyclonal T-cell responses occur following combined tumor cryotreatment and intratumoral dendritic cell administration and contribute to the observed anti-tumor immunity. In this regard, the combined treatment protected mice that had survived primary inoculation with B16-MO5 melanoma cells from re-challenge with the parental B16-F1 clone (Table 2). Given that B16-F1 cells do not express ovalbumin, and therefore are not a direct target for OT-1 T-lymphocytes, epitope spread and polyclonal T-cell responses seem to underlie the observed protection. Finally, the data in FIG. 5 demonstrated the existence of CD44$^{high}$, CD62L$^{low}$ effector memory CD8$^+$ T-lymphocytes in mice following combined cryoablation and intratumoral dendritic cell administration. Since effective mouse memory CTLs are preferably CD44$^{high}$CD62L$^{low}$, produce high levels of effector cytokines, and contain perforin (Dutton R W. et al., 1998. Annu Rev Immunol. 16:201-23; Sallusto F. et al., 1999. Nature 401:708-12), and since recent evidence has shown that cancer patient-derived memory T-cell subsets can efficiently recognize and reject autologous breast tumors (Beckhove P. et al., 2004. J Clin Invest. 114:67-76), the presently disclosed method can be used in the clinical setting to achieve efficient induction of anti-tumor memory CTLs.

Conclusion: Treatment of lethal, metastatic cancer via tumor cryoablation followed by intratumoral injection of immature dendritic cells, in contrast to either treatment type alone, was unexpectedly found to result in maximal/synergistic induction of anticancer CTLs, to uniquely result in essentially complete prevention of metastasis spread, and to uniquely result in stable, extended survival of any of the treated subjects, such extended survival being notably achieved in a large proportion (50 percent) of the treated subjects. As such, the presently disclosed novel method can be used to effectively treat cancer, such as lethal, metastatic cancer, in the clinical setting. The presently described cancer treatment method is superior to the prior art by virtue of enabling for the first time treatment of a disease, particularly a metastatic cancer, whose pathology involves a pathological cell population which is characterized by an antigen, via combined APC vaccination and localized cell ablation, in particular cryoablation, without, or with minimal, prior art chemotherapy/radiotherapy treatments, which are excessively cumbersome/complex to practice, and are associated with significantly harmful local/systemic side-effects.

Example 3

Treatment of Tumor-Bearing Mammals with Combined Tumor Cryoablation and Intratumoral Dendritic Cell Administration Specifically Induces Maximal Generation of Th1 Cytokine-Producing CD4+ T-Cells Relative to Either Treatment Alone or Combined Tumor Cryoablation and Intravenous Dendritic Cell Administration As described in Example 2 above, treatment of tumor-bearing mammals via combined tumor cryoablation and intratumoral dendritic cell administration results in optimal activation of specific anti-tumor responses, anti-metastatic effect and survival prolongation relative to either treatment alone. While reducing the present invention to practice, as described below, the present inventors have unexpectedly uncovered that combined tumor cryoablation and intratumoral dendritic cell administration induces maximal generation of Th1 cytokine producing helper T-lymphocytes relative to either treatment alone, thereby suggesting that Th1 cytokine administration can be used to increase the anti-tumor effect of the combined treatment.

Experimental Results:

Combined tumor cryoablation and intratumoral dendritic cell administration specifically induces maximal levels of Th1 cytokine-producing CD4+ T-cells relative to either treatment alone or combined tumor cryoablation and intravenous dendritic cell administration: Since type 1 and type 2 CD8+ and CD4+ T-cell responses may influence antitumor reactions, the cytokine-releasing profiles of CD4+ and CD8+ T-cells in draining lymph nodes on days 1 and 8 post-treatment were evaluated following treatment of MO5 tumor-bearing mice via cryoablation, intratumoral dendritic cell administration, combined tumor cryoablation and intratumoral dendritic cell administration or combined tumor cryoablation and intravenous dendritic cell administration. Type 1 (interferon (IFN)-gamma) and type 2 (IL-4) cytokine profiles were examined by intracellular staining and flow cytometry. The levels of CD8+ T-cells producing IFN-gamma were 2- to 3-fold higher following intratumoral dendritic cell administration treatment only or intratumoral dendritic cell administration combined with cryoablation relative to nontreated or cryotherapy treated recipients (Rehman J. et al., 2004. J. Endourol. 18:83-104). No staining for IL-4 was found in CD8+ T-cells. The proportion of CD4+ T-cells predominantly producing IFN-gamma (Th1 type) was surprisingly significantly higher in mice treated via combined cryoablation and dendritic cell administration as compared with other groups (FIG. 6). The percentage of CD4+ T-cells producing IL-4 (Th2 type) was increased in dendritic cell-treated mice and was similar to that in mice following combined treatment. These results suggests that IFN-gamma producing Th1 rather than Th2 responses were induced by treatment.

Conclusion: The presently disclosed experimental results unexpectedly demonstrate that combined tumor cryoablation and intratumoral dendritic cell administration induces maximal levels of Th1 cytokine (IFN-gamma) producing helper T-lymphocytes relative to either treatment alone, or treatment via combined tumor cryoablation and intravenous dendritic cell administration. As such these experimental results teach for the first time that intra-tumoral administration of a Th1 cytokine such as IFN-gamma can be used to increase the anti-tumor effect of treatment via combined tumor cryoablation and intratumoral dendritic cell administration.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications mentioned in this specification are herein incorporated in their entirety by reference into the specification, to the same extent as if each individual publication, patent, or patent application was specifically and individually indicated to be incorporated herein by reference. In addition, citation or identification of any reference in this application shall not be construed as an admission that such reference is available as prior art to the present invention.

What is claimed is:

1. A method of treating in a subject in need thereof a disease whose pathology involves a pathological cell population of the subject, the method comprising:
   (a) in vivo cryoablating antigen-bearing cells which comprise at least one antigen characterizing the pathological cell population, thereby generating immunogenic cells; and
   (b) administering to the subject immature dendritic cells, thereby inducing an immune response in the subject against the pathological cell population, thereby treating the disease in the subject.

2. The method of claim 1 wherein said cell population is a tumor tissue.

3. The method of claim 2 wherein the tumor tissue comprises a tumor having the potential to metastasize.

4. The method of claim 1 wherein the cell population is a population comprising cancer cells.

5. The method of claim 1 wherein the cell population comprises metastatic cancer cells.

6. The method of claim 1, further comprising:
   (c) inducing an increase in levels of Th1 cells in the subject.

7. The method of claim 1 wherein the cell population is a primary tumor tissue.

8. The method of claim 1, wherein the cell population comprises metastatic tumor cells.

9. The method of claim 1, wherein said immune response comprises generating necrotic cells and/or apoptotic cells.

10. The method of claim 1, wherein said immature dendritic cells are capable of displaying at least one antigen-presenting molecule of the subject.

11. The method of claim 1, wherein said immature dendritic cells are autologous to the subject.

12. The method of claim 1, wherein said immature dendritic cells are non-syngeneic with the subject.

13. The method of claim 1, wherein said immature dendritic cells are cultured immature dendritic cells.

14. The method of claim 1, wherein said immature dendritic cells have not been subjected to a maturation factor ex-vivo.

* * * * *

SEQUENCE LISTING

<160> NUMBER OF SEQ ID NOS: 1

<210> SEQ ID NO 1
<211> LENGTH: 8
<212> TYPE: PRT
<213> ORGANISM: Artificial sequence
<220> FEATURE:
<223> OTHER INFORMATION: H2-Kb-restricted peptide ovalbumin257-265

<400> SEQUENCE: 1

Ser Ile Ile Asn Phe Glu Lys Leu
1               5